United States Patent
Bacque et al.

(10) Patent No.: US 6,815,547 B2
(45) Date of Patent: Nov. 9, 2004

(54) QUINOLYLPROPYLPIPERIDINE DERIVATIVES, THEIR PREPARATION, AND COMPOSITIONS CONTAINING THEM

(75) Inventors: Eric Bacque, Gif sur Yvette (FR); Serge Mignani, Chatenay-Malabry (FR); Jean-Luc Malleron, Marcoussis (FR); Michel Tabart, La Norville (FR); Michel Evers, La Queue en Brie (FR); Fabrice Viviani, Louvres (FR); Youssef El Ahmad, Creteil (FR); Stéphane Mutti, Le Perreux sur Marne (FR); Christophe Daubié, Paris (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 10/387,479

(22) Filed: Mar. 14, 2003

(65) Prior Publication Data

US 2003/0171369 A1 Sep. 11, 2003

Related U.S. Application Data

(62) Division of application No. 10/096,482, filed on Mar. 13, 2002, now Pat. No. 6,602,884.
(60) Provisional application No. 60/281,407, filed on Apr. 5, 2001.

(30) Foreign Application Priority Data

Mar. 13, 2001 (FR) .............................. 01 03374

(51) Int. Cl.[7] ................... C07D 215/12; C07D 215/16; C07D 215/36
(52) U.S. Cl. ....................... 546/174; 546/177; 546/178; 546/179; 546/180
(58) Field of Search ................................. 546/174, 177, 546/178, 179, 180

(56) References Cited

U.S. PATENT DOCUMENTS

| 5,296,484 A | * | 3/1994 | Coghian et al. |
| 6,602,884 B2 | * | 8/2003 | Bacque et al. .............. 514/314 |

FOREIGN PATENT DOCUMENTS

| WO | WO 98/13350 | 4/1998 |
| WO | WO 99/37635 | 7/1999 |
| WO | WO 00/21948 | 4/2000 |
| WO | WO 00/43383 | 7/2000 |
| WO | WO 00/68199 | 11/2000 |

* cited by examiner

*Primary Examiner*—D. Margaret Seaman
(74) *Attorney, Agent, or Firm*—Finnegan, Henderson, Farabow, Garrett & Dunner, L.L.P.

(57) ABSTRACT

Quinolylpropylpiperidine derivatives of general formula (I) are described, and are useful as antimicrobial agents. Their preparation is also described.

(I)

27 Claims, No Drawings

QUINOLYLPROPYLPIPERIDINE DERIVATIVES, THEIR PREPARATION, AND COMPOSITIONS CONTAINING THEM

This application is a divisional of U.S. Application Ser. No. 10/096,482 filed Mar. 13, 2002 now U.S. Patent No. 6,602,884, which claims priority benefit of French Patent Application No. 01 03374, filed Mar. 13, 2001, and U.S. Provisional Application No. 60/281,407 filed Apr. 5, 2001, both of which are incorporated herein by reference.

One embodiment of the present invention relates to quinolyl-propylpiperidine derivatives of general formula (I):

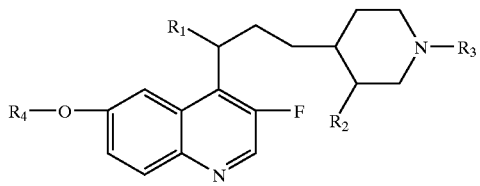

which are active as antimicrobials. Other embodiments of the invention relate to their preparation and to compositions containing them.

Patent Application Publications WO 99/37635 and WO 00/43383 describe antimicrobial quinolylpropylpiperidine derivatives of general formulas:

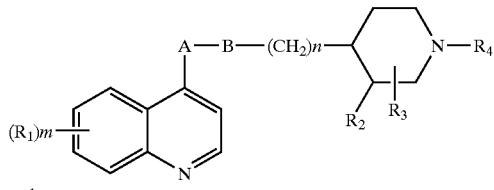

and

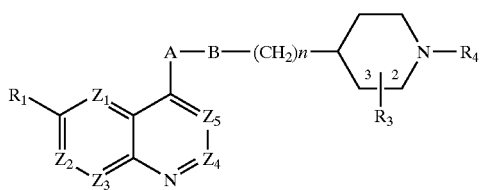

In which the radical $R_1$ may be $(C_{1-6})$alkoxy; $R_2$ is hydrogen; $R_3$ is at the 2- or 3-position and represents $(C_{1-6})$alkyl, which may be optionally substituted with 1 to 3 substituents chosen from thiol, halogen, alkylthio, trifluoromethyl, carboxyl, alkyloxycarbonyl, alkylcarbonyl, alkenyloxycarbonyl, alkenylcarbonyl, hydroxyl optionally substituted with alkyl, and the like; $R_4$ is a group —$CH_2$—$R_5$, wherein $R_5$ is selected from alkyl, hydroxyalkyl, alkenyl, alkynyl, tetrahydrofuryl, phenylalkyl, which is optionally substituted, phenylalkenyl, which is optionally substituted, heteroarylalkyl, which is optionally substituted, heteroaryl, which is optionally substituted, and the like; n is 0 to 2; m is 1 or 2; A and B may be oxygen, sulfur, sulfinyl, sulfonyl, $NR_{11}$, $CR_6R_7$, wherein $R_6$ and $R_7$ represent H, thiol, alkylthio, halo, trifluoromethyl, alkenyl, alkenylcarbonyl, hydroxyl, or amino; and $Z_1$ to $Z_5$ are N or $CR_{1a}$, and the like.

European Patent Application EP30044, describes quinoline derivatives that are useful as cardiovascular agents and that correspond to the general formula:

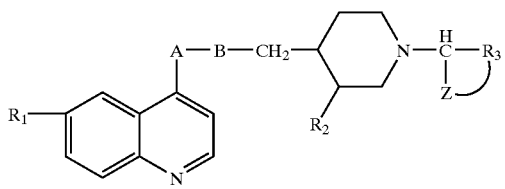

in which $R_1$ may be alkyloxy; A—B is —$CH_2$—$CH_2$—, —CHOH—$CH_2$—, —$CH_2$—CHOH—, —$CH_2$—CO— or —CO—$CH_2$—; $R_1$ is H, OH, or alkyloxy; $R_2$ is ethyl or vinyl; $R_3$ may be alkyl, hydroxyalkyl, cycloalkyl, hydroxyl, alkenyl, alkynyl, tetrahydrofuryl, phenylalkyl, diphenylalkyl, which is optionally substituted, phenylalkenyl, which is optionally substituted, benzoyl, or benzoylalkyl, which is optionally substituted, heteroaryl or heteroaryl-alkyl, which is optionally substituted; and Z is H or alkyl or forms with $R_3$ a cycloalkyl radical.

The inventors have now found that the compounds of formula (I) are potent antibacterial agents. In the compounds of formula (I), $R_1$ represents a, hydrogen atom, a halogen atom, or a hydroxyl, amino, alkylamino, dialkylamino, hydroxyamino, alkyloxyamino, or alkylalkyloxyamino radical;

$R_2$ represents a carboxyl, carboxymethyl, or hydroxymethyl radical;

$R_3$ represents an alkyl radical containing 1 to 6 carbon atoms, substituted with a phenylthio radical, which may itself carry 1 to 4 substituents chosen from halogen, hydroxyl, alkyl, alkyloxy, trifluoromethyl, trifluoro-methoxy, carboxyl, alkyloxycarbonyl, cyano, and amino, or substituted with a cycloalkylthio radical in which the cyclic portion contains 3 to 7 members, or substituted with a 5- to 6-membered aromatic heterocyclylthio radical comprising 1 to 4 heteroatoms chosen from nitrogen, oxygen, and sulfur, and itself optionally substituted with halogen, hydroxyl, alkyl, alkyloxy, trifluoromethyl, trifluoro-methoxy, oxo, carboxyl, alkyloxycarbonyl, cyano, or amino; or $R_3$ represents a propargyl radical substituted with a phenyl radical, which itself be substituted with 1 to 4 substituents chosen from halogen, hydroxyl, alkyl, alkyloxy, trifluoromethyl, trifluoromethoxy, carboxyl, alkyloxycarbonyl, cyano, and amino, or substituted with a 3- to 7-membered cycloalkyl radical or substituted with a 5- to 6-membered aromatic heterocyclyl radical comprising 1 to 4 heteroatoms chosen from nitrogen, oxygen and sulfur, and itself optionally substituted with halogen, hydroxyl, alkyl, alkyloxy, trifluoromethyl, trifluoromethoxy, oxo, carboxyl, alkyloxycarbonyl, cyano, or amino; and $R_4$ represents an alkyl radical (containing 1 to 6 carbon atoms), alkenyl-$CH_2$—, alkynyl-$CH_2$— (in which the alkenyl or alkynyl portions contain 2 to 6 carbon atoms), cycloalkyl or cycloalkylalkyl radical (in which the cycloalkyl portion contains 3 to 8 carbon atoms).

The compounds of the invention include the diastereoisomeric forms of the compounds of formula (I), their mixtures, and their cis or trans forms, as well as their salts.

It is understood that the alkyl radicals and alkyl portions of the compounds of the invention may be in the form of a straight or branched chain and contain, unless otherwise stated, 1 to 4 carbon atoms, and that in the alternative case where $R_1$ represents a halogen atom or when $R_3$ carries a halogen substituent, the latter may be chosen from fluorine, chlorine, bromine, and iodine.

Other than in the working examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of reported significant digits and by applying ordinary rounding techniques.

Notwithstanding that the numerical ranges and parameters setting forth the broad scope of the invention are approximations, the numerical values set forth in the working examples are reported as precisely as possible. Any numerical value, however, inherently contains certain errors necessarily resulting from the standard deviation found in their respective testing measurements.

In formula (I), when $R_3$ carries an aromatic heterocyclyl substituent, the latter may be chosen, without limitation, from thienyl, furyl, pyrrolyl, imidazolyl, thiazolyl, oxazolyl, thiadiazolyl, oxadiazolyl, tetrazolyl, pyridyl, pyridazinyl, pyrazinyl, and pyrimidinyl.

According to the invention, the compounds of formula (I) may be obtained by condensing an $R_3$ radical with a quinolylpropylpiperidine derivative of formula (II):

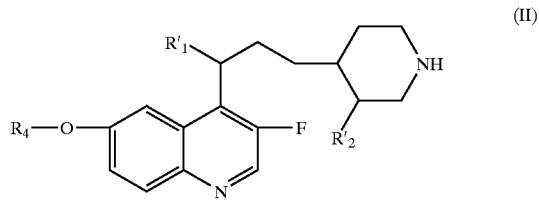

(II)

in which $R_4$ is as defined above for compounds of formula (I), $R'_1$ represents a hydrogen atom or a hydroxyl radical, and $R'_2$ represents a protected carboxyl or carboxymethyl radical, to obtain a quinolylpropylpiperidine derivative of formula (III):

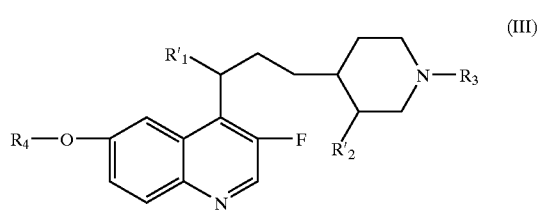

(III)

for which $R'_1$, $R'_2$, $R_3$, and $R_4$ are as defined above.

Where appropriate, this reaction may be followed by either a) the halogenation of a derivative for which $R'_1$ is a hydroxyl radical, if it is desired to obtain a quinolylpropylpiperidine derivative for which $R_1$ is a halogen atom, or b) the conversion of a hydroxyl radical to an oxo radical, and then to a hydroxyimino or alkyloxyimino radical according to known methods which do not adversely affect the rest of the molecule, to obtain a quinolylpropylpiperidine derivative of formula (IV):

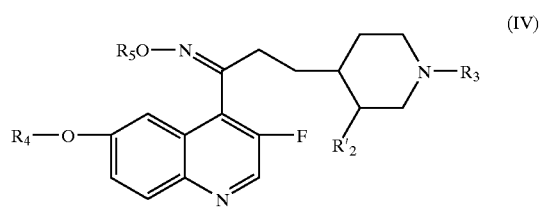

(IV)

for which $R'_2$, $R_3$, and $R_4$ are as defined above, and $R_5$ is a hydrogen atom or an alkyl radical. Where appropriate or desired, this reaction may be followed by: a) the reduction of a derivative of formula (IV) for which $R_5$ is a hydrogen atom to an amine, and optionally by the conversion to a monoalkylated or dialkylated amine; b) the reduction of the derivative of formula (IV) for which $R_5$ is a hydrogen atom to a hydroxylamine; c) the reduction of a derivative of formula (IV) for which $R_5$ is an alkyl radical to an alkyloxyamine, and then, where appropriate to obtain a derivative for which $R_1$ is alkylalkyloxy-amino, the derivative obtained for which $R_1$ is alkyl-oxyamino can be converted by alkylation, and/or d) the reduction of a protected carboxyl radical $R'_2$ to a hydroxymethyl radical according to known methods that do not adversely affect the rest of the molecule. The final step can be optionally followed by the separation of the diastereoisomers, by the separation of the cis and trans forms, by removal, where appropriate, of the acid-protecting radical, and/or by the conversion of the final reaction product obtained to a salt.

The condensation of an $R_3$ radical with piperidine may be carried out by the action of a derivative of formula (V):

$R_3$—X (V)

in which $R_3$ is as defined above and X represents a halogen atom, a methylsulfonyloxy radical, a trifluoromethylsulfonyloxy radical, or a p-toluenesulfonyloxy radical. The reaction may be carried out, for example, in an anhydrous, inert medium (nitrogen or argon, for example), in an organic solvent such as an amide (dimethylformamide, for example), a ketone (acetone, for example) or a nitrile (acetonitrile, for example) in the presence of a base such as a nitrogen-containing organic base (for example, triethylamine), or an inorganic base (alkali metal carbonate-:potassium carbonate, for example) at a temperature ranging from 20° C. to the reflux temperature of the solvent.

Examples of derivatives of formula (V) include those for which X is a bromine or an iodine atom.

When $R_3$ represents propargyl substituted with phenyl, cycloalkyl, or heterocyclyl, a propargyl halide may be condensed, and then the chain may be substituted with a phenyl, cycloalkyl, or heterocyclyl radical. In this alternative case, the addition of the propargyl chain may be carried out, for example, by means of propargyl bromide, under the conditions set out above for $R_3$ in the presence or in the absence of an alkali metal iodide such, as for example, potassium or sodium iodide.

When substitution with a phenyl or heterocyclyl radical is involved, the reaction may be carried out by the action of a halide derived from the cyclic radical to be substituted, in the presence of triethylamine, in anhydrous medium, optionally with no solvent or in a solvent such as an amide (dimethyl-formamide, for example) or a nitrite (acetonitrile, for example) and in the presence of a palladium salt such as, for example, tetrakis(triphenylphosphine)palladium and copper(I) iodide, at a temperature ranging from 20° C. to the reflux temperature of the solvent.

When substitution with a cycloalkyl group is involved, the reaction may be carried out by the action of an organolithium compound such as n-butyllithium or tert-butyllithium on the propargyl derivative obtained above, in anhydrous medium in an ether such as, for example, tetrahydrofuran at a temperature ranging from −78 to 0° C., followed by the action of a cycloalkanone and then by the deoxygenation of the intermediate alcohol according to conventional methods.

It is understood that when the alkyl radicals represented by $R_3$ carry carboxyl or amino substituents, the latter can be protected beforehand and then released after the reaction. The procedure can be carried out according to customary methods which do not adversely affect the rest of the molecule, for example, according to the methods described by T. W. Greene and P. G. M. Wuts, Protective Groups in Organic Synthesis (2nd ed.), A. Wiley—Interscience Publication (1991), or by Mc Omie, Protective Groups in Organic Chemistry, Plenum Press (1973), both of which are hereby incorporated herein by reference.

The protected carboxyl or carboxymethyl radical represented by $R'_2$ may be chosen from an easily hydrolyzable ester. These esters include, for example, methyl, benzyl, tert-butyl esters, allyl, or phenylpropyl esters. Optionally, the carboxyl radical may be protected simultaneously with the reaction. In this case, the derivative of formula (II) used carries a radical $R'_2$=carboxyl or carboxymethyl.

The halogenation intended to obtain a quinolylpropylpiperidine derivative for which $R_1$ is a halogen atom, from the derivative for which $R'_1$ is hydroxyl, may be carried out in the presence of an aminosulfur trifluoride (diethylaminosulfur trifluoride, bis(2-methoxyethyl) aminosulfur trifluoride (Deoxofluor®), or morpholinosulfur trifluoride, for example) or alternatively in the presence of sulfo tetrafluoride. The fluorination reaction may also be carried out by the action of a fluorinating agent such as a sulfur fluoride [for example, morpholinosulfur trifluoride, sulfur tetrafluoride (J. Org. Chem., 40, 3808 (1975), which is hereby incorporated by reference), diethylaminosulfur trifluoride (Tetrahedron, 44, 2875 (1988)), bis(2-methoxyethyl)aminosulfur trifluoride (Deoxofluor®). Alternatively, the fluorination reaction may also be carried out by means of a fluorinating agent such as hexafluoropropyldiethylamine (See JP 2 039 546) or N-(2-chloro-1,1,2-trifluoroethyl)diethylamine. The halogenation reaction may also be carried out using a reagent such as a tetraalkylammonium, trialkylbenzyl-ammonium, or trialkylphenylammonium halide or using an alkali metal halide optionally substituted with a crown ether.

When a tetraalkylammonium halide is used, the latter may be chosen, by way of example, from tetramethylammonium, tetraethylammonium, tetrapropylammonium, tetrabutylammonium (tetra-n-butylammonium, for example), tetrapentylammonium, tetracyclohexylammonium, triethylmethylammonium, tributylmethylammonium, and trimethylpropylammonium halides.

The procedure may be carried out in an organic solvent such as a chlorinated solvent (for example, dichloromethane, dichloroethane, or chloroform) or in an ether (tetrahydrofuran or dioxane, for example) at a temperature ranging from −78 to 40° C., for example, from 0 to 30° C.). It is advantageous to carry out the procedure in an inert medium, argon or nitrogen, for example.

It is also possible to carry out the procedure by treatment with a halogenating agent such as thionyl chloride or phosphorus trichloride in an organic solvent such as a chlorinated solvent (dichloromethane or chloroform, for example), at a temperature ranging from 0° C. to the reflux temperature of the reaction mixture.

The conversion of the hydroxyl radical to an oxo radical may be carried out using conventional oxidation methods described in the literature, such as in D. Swern oxidation, J. O. C., 44, 41–48 (1979), which is hereby incorporated by reference, for example, in the presence of oxalyl chloride and of dimethyl sulfoxide, optionally in a solvent such as dichloromethane, or without solvent, at a temperature ranging from −60 to 20° C., followed by the conversion of the oxo radical to a hydroxyimino or alkyloxyimino radical.

The conversion of the oxo radical to a hydroxyimino or alkyloxyimino radical may be carried out by the action of hydroxylamine (hydroxylamine hydrochloride, for example) or of alkyloxyamine, optionally in hydrochloride form, in a solvent such as pyridine or an alcohol (such as methanol or ethanol, for example) and in the presence of a nitrogen base such as triethylamine or pyridine at a temperature ranging from 0 to 60° C.

The reduction of a derivative of formula (IV), for which $R_5$ is hydrogen, to an amine may be carried out according to customary methods that do not adversely affect the rest of the molecule, for instance, by the action of a reducing agent such as, for example, a hydride (alkali metal borohydride, such as sodium or potassium borohydride; or aluminum and lithium hydride) in the presence or in the absence of molybdenum oxide, the procedure may be carried out under an inert atmosphere (nitrogen or argon, for example), in an organic solvent such as an alcohol (methanol, ethanol or isopropanol, for example) or a chlorinated solvent (for example, dichloromethane) at a temperature ranging from −10 to 40° C.

The reduction of a derivative of formula (IV) to a hydroxylamine or to an alkyloxyamine may be carried out, for example, in the presence of an organic acid (carboxylic acid such as, for example, acetic acid), by the action of a reducing agent such as, for example, a hydride chosen from sodium triacetoxy-borohydride (optionally prepared in situ) or sodium cyanoborohydride. In one embodiment of the invention, this reaction is carried out under an inert atmosphere (nitrogen or argon, for example), in an organic solvent such as an alcohol (methanol, ethanol or isopropanol, for example) or a chlorinated solvent (for example, dichloromethane) at a temperature ranging from −30 to +40° C.

The conversion of the amino radical represented by $R_1$ to an alkylamino or dialkylamino radical may be carried out according to customary methods, for example, by the action of an alkyl halide, optionally in a basic medium in the presence of a nitrogen base such as a trialkylamine (triethylamine, diisopropylethylamine, and the like), pyridine, or in the presence of an alkali metal hydride (sodium hydride), in an inert solvent such as an amide (dimethylformamide, for example) or an oxide (dimethyl sulfoxide, for example), at a temperature ranging from 20° C. to the reflux temperature of the reaction medium.

The conversion of the alkyloxyamino radical represented by $R_1$ to an alkylalkyloxyamino radical may be carried out according to the method described above for the alkylation of the amine.

The removal, where appropriate, of the acid-protecting radical to obtain a quinolylpropylpiperdine derivative for which $R_2$ is a carboxyl or carboxymethyl radical may be carried out according to the usual methods, for example, by acid hydrolysis or saponification of the ester $R'_2$. For instance, sodium hydroxide may be caused to act in an aqueous-organic medium, for example in an alcohol such as methanol or an ether such as dioxane, at a temperature ranging from 20° C. to the reflux temperature of the reaction mixture. It is also possible to use hydrolysis in aqueous hydrochloric medium at a temperature ranging from 20 to 100° C.

Where appropriate, a derivative of formula (I) for which $R_2$ is hydroxymethyl may be prepared from a derivative for which $R'_2$ is protected carboxyl. For example, the procedure may be carried out by reducing the product protected in the form of an ester $R'_2$, according to the customary methods that do not adversely affect the rest of the molecule, for example, by the action of a hydride (aluminum and lithium hydride or diisobutylaluminum hydride, for example) in a solvent such as an ether (tetrahydrofuran, for example) at a temperature ranging from 20 to 60° C.

A quinolylpropylpiperidine derivative of formula (II) for which $R'_2$ represents a protected carboxymethyl radical, and $R'_1$ is a hydrogen atom, may be prepared by selective hydrogenation of a quinolylpropylpiperidine derivative of formula (VI):

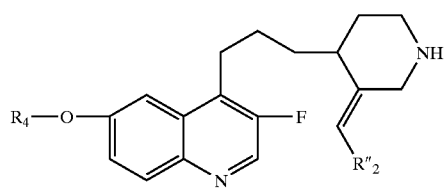

(IV)

in which $R_4$ is as defined above and $R''_2$ is the protected carboxyl radical corresponding to $R'_2$, and in which the amine functional group of the piperidine is protected beforehand, at a pressure between 1 to 100 bar and at a temperature ranging from 20 to 80° C., in a solvent such as, for example, an alcohol (ethanol, for example) or an amide (dimethylformamide, for example) in the presence of a catalyst, for example, palladium on carbon or palladium on barium sulfate.

The protection of the amino group of the piperidine may be carried out according to customary methods that do not adversely affect the rest of the molecule and that are compatible with the reaction, for example, according to the references cited above. In one embodiment of the invention, the protective radical is the benzyloxycarbonyl radical. In this case, the hydrogenation reaction leads directly to the deprotection of the amine.

A quinolylpropylpiperidine derivative of formula (VI) may be prepared by condensing a quinoline derivative of formula (VII):

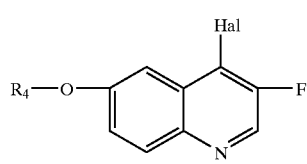

(VII)

in which $R_4$ is as defined above and Hal represents an iodine or bromine atom, with a piperidine derivative of formula (VIII):

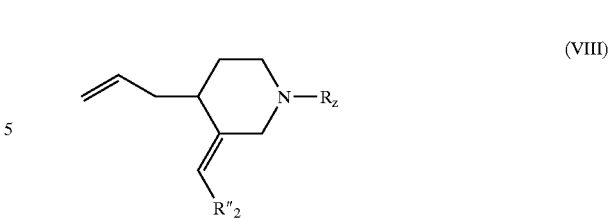

(VIII)

in which $R''_2$ is as defined above and $R_z$ represents an amino-protecting radical.

The reaction may be carried out by the successive action of an organoborane (9-borabicyclo[3.3.1]nonane, for example) in a solvent such as an ether (tetrahydrofuran or dioxane, for example) at a temperature ranging from −20 to 20° C., followed by the addition of a quinoline derivative of formula (VII), by analogy with the methods described by Suzuki et al., Pure and Appl. Chem., 57, 1749 (1985), which is hereby incorporated by reference. The reaction is generally carried out in the presence of a palladium salt (palladiumdiphenylphosphinoferrocene chloride, for example) and of a base such as potassium phosphate, at a temperature ranging from 20° C. to the reflux temperature of the solvent.

A piperidine derivative of formula (VIII) may be prepared by the Wittig reaction, by condensing a phosphorus ylide with a piperidine derivative of formula (IX):

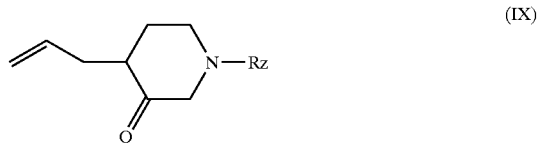

(IX)

in which Rz is as defined above.

In one embodiment of the invention, the procedure is carried out using methyl (triphenylphosphoranylidene) acetate, in a solvent such as, for example, toluene, at a temperature ranging from 20 to 110° C.

The 3-oxopiperidine derivative of formula (IX) may be prepared according to or by analogy with the method described by Y. Takeuchi et al., Synthesis, 10, 1814 (1999), which is hereby incorporated by reference.

The quinolylpropylpiperidine derivative of formula (II), for which $R'_2$ is a carboxyl radical and $R'_1$ is a hydrogen atom, may be prepared from the corresponding derivative for which $R'_2$ is protected carboxymethyl, by reducing this radical to an alcohol, converting to a p-toluenesulfonyloxy derivative, and then converting this derivative to a vinyl derivative by an elimination reaction followed by the oxidation of the derivative obtained.

According to another embodiment of the invention, a quinolylpropylpiperidine derivative of formula (II), for which $R'_2$ is a carboxyl radical and $R'_1$ is a hydrogen atom, may be prepared by condensing a quinoline derivative of formula (VII) as defined above, with a piperidine derivative of formula (X):

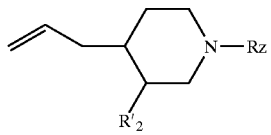

(X)

in which Rz is as defined above, and R'$_2$ represents a protected carboxyl radical as defined above, followed by removal of the amino-protecting radical Rz.

The reaction can be carried out under conditions similar to the conditions described for the reaction of the quinoline derivative of formula (VII) and of a piperidine derivative of formula (VIII). The elimination of the radical Rz can be carried out according to the methods cited above, according to the examples, or as described by T. W. Greene and P. G. M. Wuts, Protective Groups in Organic Synthesis (2nd ed.), A. Wiley-Interscience Publication (1991), or by Mc Omie, Protective Groups in Organic Chemistry, Plenum Press (1973).

A compound of formula (X) may be prepared according to or by analogy with the method described below in the examples.

The reduction, in alcohol, of the acid protected in the form of a radical R'$_2$ at the 3-position of the piperidine, to a hydroxyethyl radical can be carried out according to customary methods that do not adversely affect the rest of the molecule, for example, the procedure can be carried out by the action of a hydride (lithium and aluminum hydride or diisobutylaluminum hydride, for example) in a solvent such as an ether (tetrahydrofuran, for example) at a temperature ranging from 20 to 60° C.

The conversion of a quinolylpropyl-piperidine derivative for which R'$_2$ is hydroxyethyl to a p-toluenesulfonyloxyethyl derivative can be carried out, for example, according to the method described by L. F. Fieser and M. Fieser, Reagents for Organic Synthesis, vol. 1, 1179 (1967), which is hereby incorporated by reference, starting with p-toluenesulfonyl chloride in the presence of a base such as a tertiary amine (for example, triethylamine) or an aromatic amine (for example, pyridine), in a halogenated solvent (for example, dichloromethane) or without solvent, at a temperature ranging from 0 to 50° C.

The conversion of the p-toluenesulfonyloxy-ethyl derivative to a vinyl derivative can be carried out by an elimination reaction, for example, according to the method described by A. Sharma et al., Org. Prep Proced. Int., 25(3), 330–333 (1993), which is hereby incorporated by reference, in the presence of a base such as, for example, potassium t-butoxide in a solvent such as dimethylsulfoxide, for example, at a temperature ranging from 20 to 100° C.

The conversion of a vinyl derivative to a derivative for which R'$_2$ is carboxyl is carried out by the oxidation methods described in the literature, for example, using sodium metaperiodate in the presence of ruthenium trichloride hydrate, in a mixture of solvents such as, for example, the water/acetonitrile mixture, at a temperature ranging from 20 to 60° C.

A quinolylpropylpiperidine derivative of formula (II) for which R'$_1$ is a hydroxyl radical may be prepared by oxidizing, in a basic medium, the corresponding derivative for which R'$_1$ is a hydrogen atom. The oxidation is carried out by the action of oxygen, for example, in an inert solvent such as dimethyl sulfoxide, in the presence of tert-butanol and a base such as potassium or sodium tert-butoxide, at a temperature ranging from 0 to 100° C.

The quinoline derivatives of formula (VII) for which Hal is an iodine atom may be prepared by analogy with the work by E. Arzel et al., Tetrahedron, 55, 12149–12156 (1999), which is hereby incorporated by reference, from 3-fluoro-6-methoxyquinoline, by the successive action of a base and then of iodine. Lithium diisopropylamide may be used, for example, in a solvent such as an ether (tetrahydro-furan) at a temperature ranging from −80 to 20° C. The 3-fluoro-3-methoxyquinoline may be obtained by pyrolysis of 6-methoxyquinoline diazonium 3-tetra-fluoroborate or 3-hexafluorophosphate according to the Balz-Schieman reaction, Org. Synth., Coll 5, 133 (1973), which is hereby incorporated by reference, at a temperature ranging from 100 to 240° C. The 6-methoxyquinoline diazonium 3-tetrafluoroborate or 6-methoxyquinoline diazonium 3-hexafluorophosphate may be obtained from 3-amino-6-methoxyquinoline by the action of an alkali metal nitrite (sodium nitrite for example) in an acid medium (tetrafluoroboric acid or hexafluorophosphoric acid) in a solvent such as water, at a temperature ranging from −10 to +20° C., by analogy with the work by A. Roe et al., J. Am. Chem. Soc., 71, 1785–86 (1949), which is hereby incorporated by reference or by the action of an alkyl nitrite (such as, for example, isoamyl nitrite) and of the complex of diethyl ether trifluoroborate in a solvent such as an ether (tetrahydrofuran, for example) at a temperature ranging from −10 to +10° C. The 3-amino-6-methoxyquinoline can be prepared as described by N. Heindel, J. Med. Chem., 13, 760 (1970), which is hereby incorporated by reference. The quinoline derivative of formula (VII) for which Hal is a bromine atom may also be prepared by analogy with this method.

The intermediates of the quinolylpropyl-piperidine derivatives for which R$_4$ represents alkenyl-CH$_2$—, alkynyl-CH$_2$—, cycloalkyl or cycloalkyl-alkyl may be obtained by analogy with the preparation of the intermediates for which R$_4$ is alkyl, by the action of the corresponding halogenated derivative on the quinoline derivative hydroxylated at the 6-position.

It is understood that the derivatives of formula (I), (II), (III), (IV) and their starting intermediates may exist in the cis or trans form at the level of the substituents at the 3- and 4-position of piperidine. The derivatives of the trans configuration may be obtained from the derivatives of the cis configuration according to or by analogy with the method described in International Application WO 99/37635, which method is hereby incorporated by reference.

The quinolylpropylpiperdine derivatives of formula (I) may be purified, where appropriate, by physical methods such as crystallization or chromatography.

Moreover, it is understood that when R$_1$ is other than a hydrogen atom, diastereoisomeric forms may exist and that the diastereoisomeric forms and mixtures thereof also fall within the scope of the present invention. Diastereoisomeric mixtures may be separated, for example, by chromatography on silica or by High-Performance Liquid Chromatography (HPLC). Likewise, the cis and trans derivatives may be separated by chromatography on silica or by High-Performance Liquid Chromatography (HPLC).

The quinolylpropylpiperidine derivatives of formula (I) may be converted to addition salts with acids by known methods. It is understood that these salts also fall within the scope of the present invention.

Examples of addition salts with pharmaceutically acceptable acids include the salts formed with inorganic acids (for example, hydrochlorides, hydrobromides, sulfates, nitrates, and phosphates) or with organic acids (for example, succinates, fumarates, tartrates, acetates, propionates, maleates, citrates, methanesulfonates, ethanesulfonates, phenyl-sulfonates, p-toluenesulfonates, isethionates, naphthylsulfonates, and camphorsulfonates, or with the substitution derivatives of these compounds).

Some of the quinolylpropylpiperidine derivatives of formula (I) carrying a carboxyl radical may be converted to the form of metal salts or to addition salts with the nitrogen bases according to methods known per se. These salts also fall within the scope of the present invention. The salts may be obtained by the action of a metal base (for example, an alkali or alkaline-earth metal), ammonia or an amine, on a product according to the invention, in an appropriate solvent such as an alcohol, an ether, or water, or by an exchange reaction with a salt of an organic acid. The salt formed precipitates after optional concentration of the solution, it may be separated by filtration, decantation, or freeze-drying. Examples of pharmaceutically acceptable salts include the salts formed with alkali metals (sodium, potassium, lithium) or alkaline-earth metals (magnesium, calcium), the ammonium salt, and the salts of nitrogen bases (ethanolamine, diethanolamine, trimethylamine, triethylamine, methylamine, propylamine, diisopropylamine, N,N-dimethylethanol-amine, benzylamine, dicyclohexylamine, N-benzyl-β-phenethylamine, N,N'-dibenzylethylenediamine, diphenylenediamine, benzhydrylamine, quinine, chloline, arginine, lysine, leucine, and dibenzylamine).

The quinolylpropylpiperidine derivatives according to the invention are useful advantageous antibacterial agents.

In vitro, on gram-positive microbes, the quinolylpropylpiperidine derivatives according to the invention have proved active at concentrations ranging from 0.03 to 4 μg/ml on meticillin-resistant *Staphylococcus aureus* AS5155, also at concentrations ranging from 0.06 to 8 μg/ml on *Streptococcus pneumoniae* 6254-01 and at concentrations ranging from 0.06 to 64 μg/ml on *Enterococcus faecium* H983401. On gram-negative microbes they have proved active at concentrations ranging from 0.32 to 32 μg/ml on *Moraxella catharrhalis* IPA152; in vivo, they have proved active on experimental infections of mice with *Straphylococcus aureus* IP8203 at doses ranging from 12 to 150 mg/kg by the subcutaneous route (CD50) and for some of them at doses ranging from 26 to 150 mg/kg by the oral route.

Finally, the compounds according to the invention are also useful, because of their low toxicity to the host. None of the compounds exhibited toxicity at the dose of 100 mg/kg by the subcutaneous route in mice (2 administrations).

Examples of the quinolylpropylquinoline derivatives of the invention include:

(3RS,4RS) or (3SR,4RS)-4-[3-(3-fluoro-6-methoxyquinolin-4-yl)propyl]-1-(2-phenylthioethyl)piperidine-3-carboxylic acid (3RS,4RS) or (3SR,4RS)-4-[3-(3-fluoro-6-methoxyquinolin-4-yl)propyl]-1-[2-(3-fluorophenylthio)ethyl]piperidine-3-carboxylic acid (3RS,4RS) or (3SR,4RS)-4-[3-(3-fluoro-6-methoxyquinolin-4-yl)propyl]-1-[2-(2,5-difluorophenylthio)ethyl]piperidine-3-carboxylic acid (3RS,4RS) or (3SR,4RS)-4-[3-(3-fluoro-6-methoxyquinolin-4-yl)propyl]-1-[2-(3,5-difluorophenylthio)ethyl]piperidine-3-carboxylic acid (3RS,4RS) or (3SR,4RS)-4-[3-(3-fluoro-6-methoxyquinolin-4-yl)propyl]-1-[2-(2,3,5-trifluorophenylthio)ethyl]piperidine-3-carboxylic acid (3RS,4RS) or (3SR,4RS)-4-[3-(3-fluoro-6-methoxyquinolin-4-yl)propyl]-1-[3-(n-propylthio)propyl]piperidine-3-carboxylic acid (3RS,4RS) or (3SR,4RS)-4-[3-(3-fluoro-6-methoxyquinolin-4-yl)propyl]-1-[2-(n-butylthio)ethyl]piperidine-3-carboxylic acid (3RS,4RS) or (3SR,4RS)-4-[3-(3-fluoro-6-methoxyquinolin-4-yl)propyl]-1-[2-(cyclopropylthio)ethyl]piperidine-3-carboxylic acid (3RS,4RS) or (3SR,4RS)-4-[3-(3-fluoro-6-methoxyquinolin-4-yl)propyl]-1-[2-(cyclobutylthio)ethyl]piperidine-3-carboxylic acid (3RS,4RS) or (3SR,4RS)-4-[3-(3-fluoro-6-methoxyquinolin-4-yl)propyl]-1-[2-(cyclopentylthio)ethyl]piperidine-3-carboxylic acid (3RS,4RS) or (3SR,4RS)-4-[3-(3-fluoro-6-methoxyquinolin-4-yl)propyl]-1-[2-(cyclohexylthio)ethyl]piperidine-3-carboxylic acid (3RS,4RS) or (3SR,4RS)-4-[3-(3-fluoro-6-methoxyquinolin-4-yl)propyl]-1-[2-(thien-2-yl)thioethyl]piperidine-3-carboxylic acid (3RS,4RS) or (3SR,4RS)-4-[3-(3-fluoro-6-methoxyquinolin-4-yl)propyl]-1-[2-(5-fluorothien-2-yl)thioethyl]piperidine-3-carboxylic acid (3RS,4RS) or (3SR,4RS)-4-[3-(3-fluoro-6-methoxyquinolin-4-yl)propyl]-1-[2-(thien-3-yl)thioethyl]piperidine-3-carboxylic acid (3RS,4RS) or (3SR,4RS)-4-[3-(3-fluoro-6-methoxyquinolin-4-yl)propyl]-1-[2-(1,3-thiazol-2-yl)thioethyl]piperidine-3-carboxylic acid (3RS,4RS) or (3SR,4RS)-4-[3-(3-fluoro-6-methoxyquinolin-4-yl)propyl]-1-[2-(pyridin-2-yl)thioethyl]piperidine-3-carboxylic acid (3RS,4RS) or (3SR,4RS)-4-[3-(3-fluoro-6-methoxyquinolin-4-yl)propyl]-1-[2-(3-fluoropyridin-2-yl)thioethyl]piperidine-3-carboxylic acid (3RS,4RS) or (3SR,4RS)-4-[3-(3-fluoro-6-methoxyquinolin-4-yl)propyl]-1-[3-(3-fluorophenyl)prop-2-ynyl]piperidine-3-carboxylic acid (3RS,4RS) or (3SR,4RS)-4-[3-(3-fluoro-6-methoxyquinolin-4-yl)propyl]-1-[3-(2,5-difluorophenyl)prop-2-ynyl]piperidine-3-carboxylic acid (3RS,4RS) or (3SR,4RS)-4-[3-(3-fluoro-6-methoxyquinolin-4-yl)propyl]-1-[3-(3,5-difluorophenyl)prop-2-ynyl]-piperidine-3-carboxylic acid (3RS,4RS) or (3SR,4RS)-4-[3-(3-fluoro-6-methoxyquinolin-4-yl)propyl]-1-[3-(2,3,5-trifluorophenyl)prop-2-ynyl]piperidine-3-carboxylic acid (3RS,4RS) or (3SR,4RS)-4-[3-(3-fluoro-6-methoxyquinolin-4-yl)propyl]-1-[3-(thien-2-yl)prop-2-ynyl]piperidine-3-carboxylic acid (3RS,4RS) or (3SR,4RS)-4-[3-(3-fluoro-6-methoxyquinolin-4-yl)propyl])1-[3-(thien-3-yl)prop-2-ynyl]piperidine-3-carboxylic acid (3RS,4RS) or (3SR,4RS)-4-[3-(R,S)-hydroxy-3-(3-fluoro-6-methoxyquinolin-4-yl)propyl]-1-(2-phenylthioethyl)piperidine-3-carboxylic acid (3RS,4RS) or (3SR,4RS)-4-[3-(R,S)-hydroxy-3-(3-fluoro-6-methoxyquinolin-4-yl)propyl]-1-[2-(3-fluorophenylthio)ethyl]piperidine-3-carboxylic acid (3RS,4RS) or (3SR,4RS)-4-[3-(R,S)-hydroxy-3-(3-fluoro-6-methoxyquinolin-4-yl)propyl]-1-[2-(2,5-difluorophenylthio)ethyl]piperidine-3-carboxylic acid (3RS,4RS) or (3SR,4RS)-4-[3-(R,S)-hydroxy-3-(3-fluoro-6-methoxyquinolin-4-yl)propyl]-1-[2-(3,5-difluorophenylthio)ethyl]piperidine-3-carboxylic acid (3RS,4RS) or (3SR,4RS)-4-[3-(R,S)-hydroxy-3-(3-fluoro-6-methoxyquinolin-4-yl)propyl]-1-[2-(2,3,5-trifluorophenylthio)ethyl]piperidine-3-carboxylic acid (3RS,4RS) or (3SR,4RS)-4-[3-(R,S)-hydroxy-3-(3-fluoro-6-methoxyquinolin-4-yl)propyl]-1-[3-(n-propylthio)ethyl]piperidine-3-carboxylic acid (3RS,4RS) or (3SR,4RS)-4-[3-(R,S)-hydroxy-3-(3-fluoro-6-methoxyquinolin-4-yl)propyl]-1-[2-(n-butylthio)ethyl]piperidine-3-carboxylic acid (3RS,4RS) or (3SR,4RS)-4-[3-(R,S)-hydroxy-3-(3-fluoro-6-methoxyquinolin-4-yl)propyl]-1-[2-(cyclopropylthio)ethyl]piperidine-3-carboxylic acid (3RS,4RS) or (3SR,4RS)-4-[3-(R,S)-hydroxy-3-(3-fluoro-6-methoxyquinolin-4-yl)propyl]-1-[2-(cyclobutylthio)ethyl]piperidine-3-carboxylic acid (3RS,4RS) or (3SR,4RS)-4-[3-(R,S)-hydroxy-3-(3-fluoro-6-methoxyquinolin-4-yl)propyl]-1-[2-(cyclopentylthio)ethyl]piperidine-3-carboxylic acid (3RS,4RS) or (3SR,4RS)-4-[3-(R,S)-hydroxy-3-(3-fluoro-6-methoxyquinolin-4-yl)propyl]-1-[2-(cyclohexylthio)ethyl]piperidine-3-carboxylic acid (3RS,4RS) or (3SR,4RS)-4-[3-(R,S)-hydroxy-3-(3-fluoro-6-methoxyquinolin-4-yl)propyl]-1-[2-(5-fluorothien-2-yl)thioethyl]piperidine-3-carboxylic acid (3RS,4RS) or (3SR,4RS)-4-[3-(R,S)-hydroxy-3-(3-fluoro-6-methoxyquinolin-4-yl)propyl]-1-[2-(thien-3-yl)thioethyl]piperidine-3-carboxylic acid (3RS,4RS) or (3SR,4RS)-4-[3-(R,S)-hydroxy-3-(3-fluoro-6-methoxyquinolin-4-yl)propyl]-1-[2-(1,3-thiazol-2-yl)thioethyl]piperidine-3-carboxylic acid (3RS,4RS) or (3S,4RS)-4-[3-(R,S)-hydroxy-3-(3-fluoro-6-methoxyquinolin-4-yl)propyl]-1-[2-(3-fluoropyridin-2-yl)thioethyl]piperidine-3-carboxylic acid (3RS,4RS) or (3SR,4RS)-4-[3-(R,S)-hydroxy-3-(3-fluoro-6-methoxyquinolin-4-yl)propyl]-1-[2-(pyridin-2-yl)thioethyl]piperidine-3-carboxylic acid (3RS,4RS) or (3SR,4RS)-4-[3-(R,S)-hydroxy-3-(3-fluoro-6-methoxyquinolin-4-yl)propyl]-1-[3-(3-fluorophenyl)prop-2-ynyl]piperidine-3-carboxylic acid (3RS,4RS) or (3SR,4RS)-4-[3-(R,S)-hydroxy-3-(3-fluoro-6-methoxyquinolin-4-yl)propyl]-1-[3-(2,5-difluorophenyl)prop-2-ynyl]-piperidine-3-carboxylic acid (3RS,4RS) or (3SR,4RS)-4-[3-(R,S)-hydroxy-3-(3-fluoro-6-methoxyquinolin-4-yl)propyl]-1-[3-(3,5-difluorophenyl)prop-2-ynyl]piperidine-3-carboxylic acid (3RS,4RS) or (3SR,4RS)-4-[3-(R,S)-hydroxy-3-(3-fluoro-6-methoxyquinolin-4-yl)propyl]-1-[3-(2,3,5-trifluorophenyl)prop-2-ynyl]piperidine-3-carboxylic acid (3RS,4RS) or (3SR,4RS)-4-[3-(R,S)-hydroxy-3-(3-fluoro-6-methoxyquinolin-4-yl)propyl]-1-[3-(thien-2-yl)prop-2-ynyl]piperidine-3-carboxylic acid (3RS,4RS) or (3SR,4RS)-4-[3-(R,S)-hydroxy-3-(3-fluoro-6-methoxyquinolin-4-yl)propyl]-1-[3-(thien-3-yl)prop-2-ynyl]piperidine-3-carboxylic acid (3RS,4RS) or (3SR,4RS)-4-[3-(R,S)-fluoro-3-(3-fluoro-6-methoxyquinolin-4-yl)propyl]-1-[2-(2,5-difluorophenylthio)ethyl]piperidine-3-carboxylic acid (3RS,4RS) or (3SR,4RS)-4-[3-(R,S)-fluoro-3-(3-fluoro-6-methoxyquinolin-4-yl)propyl]-1-[2-(3,5-difluorophenylthio)ethyl]piperidine-3-carboxylic acid (3RS,4RS) or (3SR,4RS)-4-[3-(R,S)-fluoro-3-(3-fluoro-6-methoxyquinolin-4-yl)propyl]-1-[2-(cyclopentylthio)ethyl]piperidine-3-carboxylic acid (3RS,4RS) or (3SR,4RS)-4-[3-(R,S)-fluoro-3-(3-fluoro-6-methoxyquinolin-4-yl)propyl]-1-[2-(cyclohexylthio)ethyl]piperidine-3-carboxylic acid (3RS,4RS) or (3SR,4RS)-4-[3-(R,S)-fluoro-3-(3-fluoro-6-methoxyquinolin-4-yl)propyl]-1-[2-(thien-2-yl)thioethyl]piperidine-3-carboxylic acid (3RS,4RS) or (3SR,4RS)-4-[3-(R,S)-fluoro-3-(3-fluoro-6-methoxyquinolin-4-yl)propyl]-1-[2-(1,3-thiazol-2-yl)thioethyl]piperidine-3-carboxylic acid (3RS,4RS) or (3SR,4RS)-4-[3-(R,S)-fluoro-3-(3-fluoro-6-methoxyquinolin-4-yl)propyl]-1-[2-(pyridin-2-yl)thioethyl]piperidine-3-carboxylic acid (3RS,4RS) or (3SR,4RS)-4-[3-(R,S)-fluoro-3-(3-fluoro-6-methoxyquinolin-4-yl)propyl]-1-[3-(3,5-difluorophenyl)prop-2-ynyl]piperidine-3-carboxylic acid (3RS,4RS) or (3SR,4RS)-4-[3-(R,S)-fluoro-3-(3-fluoro-6-methoxyquinolin-4-yl)propyl]-1-[3-(2,3,5-trifluorophenyl)prop-2-ynyl]piperidine-3-carboxylic acid (3RS,4RS) or (3SR,4RS)-4-[3-(R,S)-fluoro-3-(3-fluoro-6-methoxyquinolin-4-yl)propyl]-1-[3-(thien-2-yl)prop-2-ynyl]piperidine-3-carboxylic acid (3RS,4RS) or (3SR,4RS)-4-[3-(R,S)-amino-3-(3-fluoro-6-methoxyquinolin-4-yl)propyl]-1-(2-phenylthioethyl)piperidine-3-carboxylic acid (3RS,4RS) or (3SR,4RS)-4-[3-(R,S)-amino-3-(3-fluoro-6-methoxyquinolin-4-yl)propyl]-1-[2-(3-fluorophenylthio)ethyl]piperidine-3-carboxylic acid (3RS,4RS) or (3SR,4RS)-4-[3-(R,S)-amino-3-(3-fluoro-6-methoxyquinolin-4-yl)propyl]-1-[2-(2,5-difluorophenylthio)ethyl]piperidine-3-carboxylic acid (3RS,4RS) or (3SR,4RS)-4-[3-(R,S)-amino-3-(3-fluoro-6-methoxyquinolin-4-yl)propyl]-1-[2-(3,5-difluorophenylthio)ethyl]piperidine-3-carboxylic acid (3RS,4RS) or (3SR,4RS)-4-[3-(R,S)-amino-3-(3-fluoro-6-methoxyquinolin-4-yl)propyl]1-[2-(2,3,5-trifluorophenylthio)ethyl]piperidine-3-carboxylic acid (3RS,4RS) or (3SR,4RS)-4-[3-(R,S)-amino-3-(3-fluoro-6-methoxyquinolin-4-yl)propyl]-1-[3-(n-propylthio)propyl]piperidine-3-carboxylic acid (3RS,4RS) or (3SR,4RS)-4-[3-(R,S)-amino-3-(3-fluoro-6-methoxyquinolin-4-yl)propyl]-1-[2-(n-butylthio)ethyl]piperidine-3-carboxylic acid (3RS,4RS) or (3SR,4RS)-4-[3-(R,S)-amino-3-(3-fluoro-6-methoxyquinolin-4-yl)propyl]-1-[2-(cyclopropylthio)ethyl]piperidine-3-carboxylic acid (3RS,4RS) or (3SR,4RS)-4-[3-(R,S)-amino-3-(3-fluoro-6-methoxyquinolin-4-yl)propyl]-1-[2-(cyclobutylthio)ethyl]piperidine-3-carboxylic acid (3RS,4RS) or (3SR,4RS)-4-[3-(R,S)-amino-3-(3-fluoro-6-methoxyquinolin-4-yl)propyl]-1-[2-(cyclopentylthio)ethyl]piperidine-3-carboxylic acid (3RS,4RS) or (3SR,4RS)-4-[3-(R,S)-amino-3-(3-fluoro-6-methoxyquinolin-4-yl)propyl]-1-[2-(cyclohexylthio)ethyl]piperidine-3-carboxylic acid (3RS,4RS) or (3SR,4RS)-4-[3-(R,S)-amino-3-(3-fluoro-6-methoxyquinolin-4-yl)propyl]-1-[2-(thien-2-yl)thioethyl]piperidine-3-carboxylic acid (3RS,4RS) or (3SR,4RS)-4-[3-(R,S)-amino-3-(3-fluoro-6-methoxyquinolin-4-yl)propyl]-1-[2-(5-fluorothien-2-yl)thioethyl]piperidine-3-carboxylic acid (3RS,4RS) or (3SR,4RS)-4-[3-(R,S)-amino-3-(3-fluoro-6-methoxyquinolin-4-yl)propyl]-1-[2-(thien-3-yl)thioethyl]piperidine-3-carboxylic acid (3RS,4RS) or (3SR,4RS)-4-[3-(R,S)-amino-3-(3-fluoro-6-methoxyquinolin-4-yl)propyl]-1-[2-(1,3-thiazol-2-yl)thioethyl]piperidine-3-carboxylic acid (3RS,4RS) or (3SR,4RS)-4-[3-(R,S)-amino-3-(3-fluoro-6-methoxyquinolin-4-yl)propyl]-1-[2-(pyridin-2-yl)thioethyl]piperidine-3-carboxylic acid (3RS,4RS) or (3SR,4RS)-4-[3-(R,S)-amino-3-(3-fluoro-6-methoxyquinolin-4-yl)propyl]-1-[2-(pyridin-3-yl)thioethyl]piperidine-3-carboxylic acid (3RS,4RS) or (3SR,4RS)-4-[3-(R,S)-amino-3-(3-fluoro-6-methoxyquinolin-4-yl)propyl]-1-[3-(3-fluorophenyl)prop-2-ynyl]piperidine-3-carboxylic acid (3RS,4RS) or (3SR,4RS)-4-[3-(R,S)-amino-3-(3-fluoro-6-methoxyquinolin-4-yl)propyl]-1-[3-(2,5-difluorophenyl)prop-2-ynyl]piperidine-3-carboxylic acid (3RS,4RS) or (3SR,4RS)-4-[3-(R,S)-amino-3-(3-fluoro-6-methoxyquinolin-4-yl)propyl]-1-[3-(3,5-difluorophenyl)prop-2-ynyl]piperidine-3-carboxylic acid (3RS,4RS) or (3SR,4RS)-4-[3-(R,S)-amino-3-(3-fluoro-6-methoxyquinolin-4-yl)propyl]-1-[3-(2,3,5-trifluorophenyl)prop-2-ynyl]piperidine-3-carboxylic acid (3RS,4RS) or (3SR,4RS)-4-[3-(R,S)-amino-3-(3-fluoro-6-methoxyquinolin-4-yl)propyl]-1-[3-(thien-2-yl)prop-2-ynyl]piperidine-3-carboxylic acid (3RS,4RS) or (3SR,4RS)-4-[3-(R,S)-amino-3-(3-fluoro-6-methoxyquinolin-4-yl)propyl]-1-[3-(thien-3-yl)-prop-2-ynyl]piperidine-3-carboxylic acid (3RS,4RS) or (3SR,4RS)-4-[3-(3-fluoro-6-methoxyquinolin-4-yl)propyl]-1-(2-phenylthioethyl)piperidine-3-acetic acid (3RS,4RS) or (3SR,4RS)-4-[3-(3-fluoro-6-methoxyquinolin-4-yl)propyl]-1-[2-(3-fluorophenylthio)ethyl]piperidine-3-acetic acid (3RS,4RS) or (3SR,4RS)-4-[3-(3-fluoro-6-methoxyquinolin-4-yl)propyl]-1-[2-(2,5-difluorophenylthio)ethyl]piperidine-3-acetic acid (3RS,4RS) or (3SR,4RS)-4-[3-(3-fluoro-6-methoxyquinolin-4-yl)propyl]-1-[2-(3,5-difluorophenylthio)ethyl]piperidine-3-acetic acid (3RS,4RS) or (3SR,4RS)-4-[3-(3-fluoro-6-methoxyquinolin-4-yl)propyl]-1-[2-(2,3,5-trifluorophenylthio)ethyl]piperidine-3-acetic acid (3RS,4RS) or (3SR,4RS)-4-[3-(3-fluoro-6-methoxyquinolin-4-yl)propyl]-1-[3-(n-propylthio)propyl]piperidine-3-acetic acid (3RS,4RS) or (3SR,4RS)-4-[3-(3-fluoro-6-methoxyquinolin-4-yl)propyl]-1-[2-(n-butylthio)ethyl]piperidine-3-acetic acid (3RS,4RS) or (3SR,4RS)-4-[3-(3-fluoro-6-methoxyquinolin-4-yl)propyl]-1-[2-(cyclopropylthio)ethyl]piperidine-3-acetic acid (3RS,4RS) or (3SR,4RS)-4-[3-(3-fluoro-6-methoxyquinolin-4-yl)propyl]-1-[2-(cyclobutylthio)ethyl]piperidine-3-acetic acid (3RS,4RS) or (3SR,4RS)-4-[3-(3-fluoro-6-methoxyquinolin-4-yl)propyl]-1-[2-(cyclopentylthio)ethyl]piperidine-3-acetic acid (3RS,4RS) or (3SR,4RS)-4-[3-(3-fluoro-6-methoxyquinolin-4-yl)propyl]-1-[2-(cyclohexylthio)ethyl]piperidine-3-acetic acid (3RS,4RS) or (3SR,4RS)-4-[3-(3-fluoro-6-methoxyquinolin-4-yl)propyl]-1-[2-(5-fluoro-thien-2-yl)thioethyl]piperidine-3-acetic acid (3RS,4RS) or (3SR,4RS)-4-[3-(3-fluoro-6-methoxyquinolin-4-yl)propyl]-1-[2-(thien-3-yl)thioethyl]piperidine-3-acetic acid (3RS,4RS) or (3SR,4RS)-4-[3-(3-fluoro-6-methoxyquinolin-4-yl)propyl]-1-[2-(1,3-thiazol-2-yl)thioethyl]piperidine-3-acetic acid (3RS,4RS) or (3SR,4RS)-4-[3-(3-fluoro-6-methoxyquinolin-4-yl)propyl]-1-[2-(pyridin-2-yl)thioethyl]piperidine-3-acetic acid (3RS,4RS) or (3SR,4RS)-4-[3-(3-fluoro-6-methoxyquinolin-4-yl)propyl]-1-[2-(3-fluoropyridin-2-yl)thioethyl]piperidine-3-acetic acid (3RS,4RS) or (3SR,4RS)-4-[3-(3-fluoro-6-methoxyquinolin-4-yl)propyl]-1-[3-(3-fluorophenyl)prop-2-ynyl]piperidine-3-acetic acid (3RS,4RS) or (3SR,4RS)-4-[3-(3-fluoro-6-methoxyquinolin-4-yl)propyl]-1-[3-(3,5-difluorophenyl)prop-2-ynyl]piperidine-3-acetic acid (3RS,4RS) or (3SR,4RS)-4-[3-(3-fluoro-6-methoxyquinolin-4-yl)propyl]-1-[3-(2,5-difluorophenyl)prop-2-ynyl]piperidine-3-acetic acid (3RS,4RS) or (3SR,4RS)-4-[3-(3-fluoro-6-methoxyquinolin-4-yl)propyl]-1-[3-(2,3,5-trifluorophenyl)prop-2-ynyl]piperidine-3-acetic acid (3RS,4RS) or (3SR,4RS)-4-[3-(3-fluoro-6-methoxyquinolin-4-yl)propyl]-1-[3-(thien-2-yl)prop-2-ynyl]piperidine-3-acetic acid (3RS,4RS) or (3SR,4RS)-4-[3-(3-fluoro-6-methoxyquinolin-4-yl)propyl]-1-[3-(thien-3-yl)prop-2-ynyl]piperidine-3-acetic acid (3RS,4RS) or (3SR,4RS)-4-[3-(R,S)-hydroxy-3-(3-fluoro-6-methoxyquinolin-4-yl)propyl]-1-(2-phenylthioethyl)piperidine-3-acetic acid (3RS,4RS) or (3SR,4RS)-4-[3-(R,S)-hydroxy-3-(3-fluoro-6-methoxyquinolin-4-yl)propyl]-1-[2-(3-fluorophenylthio)ethyl]piperidine-3-acetic acid (3RS,4RS) or (3SR,4RS)-4-[3-(R,S)-hydroxy-3-(3-fluoro-6-methoxyquinolin-4-yl)propyl]-1-[2-(3,5-difluorophenylthio)ethyl]piperidine-3-acetic acid (3RS,4RS) or (3SR,4RS)-4-[3-(R,S)-hydroxy-3-(3-fluoro-6-methoxyquinolin-4-yl)propyl]-1-[2-(2,3,5-trifluorophenylthio)ethyl]piperidine-3-acetic acid (3RS,4RS) or (3SR,4RS)-4-[3-(R,S)-hydroxy-3-(3-fluoro-6-methoxyquinolin-4-yl)propyl]-1-[3-(n-propylthio)propyl]piperidine-3-acetic acid (3RS,4RS) or (3SR,4RS)-4-[3-(R,S)-hydroxy-3-(3-fluoro-6-methoxyquinolin-4-yl)propyl]-1-[2-(n-butylthio)ethyl]piperidine-3-acetic acid (3RS,4RS) or (3SR,4RS)-4-[3-(R,S)-hydroxy-3-(3-fluoro-6-methoxyquinolin-4-yl)propyl]-1-[2-(cyclopropylthio)ethyl]piperidine-3-acetic acid (3RS,4RS) or (3SR,4RS)-4-[3-(R,S)-hydroxy-3-(3-fluoro-6-methoxyquinolin-4-yl)propyl]-1-[2-(cyclobutylthio)ethyl]piperidine-3-acetic acid (3RS,4RS) or (3SR,4RS)-4-[3-(R,S)-hydroxy-3-(3-fluoro-6-methoxyquinolin-4-yl)propyl]-1-[2-(cyclohexylthio)ethyl]piperidine-3-acetic acid (3RS,4RS) or (3SR,4RS)-4-[3-(R,S)-hydroxy-3-(3-fluoro-6-methoxyquinolin-4-yl)propyl]-1-[2-(5-fluorothien-2-yl)thioethyl]piperidine-3-acetic acid (3RS,4RS) or (3SR,4RS)-4-[3-(R,S)-hydroxy-3-(3-fluoro-6-methoxyquinolin-4-yl)propyl]-1-[2-(thien-3-yl)thioethyl]piperidine-3-acetic acid (3RS,4RS) or (3SR,4RS)-4-[3-(R,S)-hydroxy-3-(3-fluoro-6-methoxyquinolin-4-yl)propyl]-1-[2-(1,3-thiazol-2-yl)thioethyl]piperidine-3-acetic acid (3RS,4RS) or (3SR,4RS)-4-[3-(R,S)-hydroxy-3-(3-fluoro-6-methoxyquinolin-4-yl)propyl]-1-[2-(pyridin-2-yl)thioethyl]piperidine-3-acetic acid (3RS,4RS) or (3SR,4RS)-4-[3-(R,S)-hydroxy-3-(3-fluoro-6-methoxyquinolin-4-yl)propyl]-1-[2-(3-fluoropyridin-2-yl)thioethyl]piperidine-3-acetic acid (3RS,4RS) or (3SR,4RS)-4-[3-(R,S)-hydroxy-3-(3-fluoro-6-methoxyquinolin-4-yl)propyl]-1-[3-(3-fluorophenyl)prop-2-ynyl]piperidine-3-acetic acid (3RS,4RS) or (3SR,4RS)-4-[3-(R,S)-hydroxy-3-(3-fluoro-6-methoxyquinolin-4-yl)propyl]-1-[3-(3,5-difluorophenyl)prop-2-ynyl]piperidine-3-acetic acid (3RS,4RS) or (3SR,4RS)-4-[3-(R,S)-hydroxy-3-(3-fluoro-6-methoxyquinolin-4-yl)propyl]-1-[3-(2,5-difluorophenyl)prop-2-ynyl]piperidine-3-acetic acid (3RS,4RS) or (3SR,4RS)-4-[3-(R,S)-hydroxy-3-(3-fluoro-6-methoxyquinolin-4-yl)propyl]-1-[3-(thien-2-yl)prop-2-ynyl]piperidine-3-acetic acid (3RS,4RS) or (3SR,4RS)-4-[3-(R,S)-hydroxy-3-(3-fluoro-6-methoxyquinolin-4-yl)propyl]-1-[3-(thien-3-yl)prop-2-ynyl]piperidine-3-acetic acid (3RS,4RS) or (3SR,4RS)-4-[3-(R,S)-fluoro-3-(3-fluoro-6-methoxyquinolin-4-yl)propyl]-1-[2-(2,5-difluorophenylthio)ethyl]piperidine-3-acetic acid (3RS,4RS) or (3SR,4RS)-4-[3-(R,S)-fluoro-3-(3-fluoro-6-methoxyquinolin-4-yl)propyl]-1-[2-(3,5-difluorophenylthio)ethyl]piperidine-3-acetic acid (3RS,4RS) or (3SR,4RS)-4-[3-(R,S)-fluoro-3-(3-fluoro-6-methoxyquinolin-4-yl)propyl]-1-[2-(cyclopentylthio)ethyl]piperidine-3-acetic acid (3RS,4RS) or (3SR,4RS)-4-[3-(R,S)-fluoro-3-(3-fluoro-6-methoxyquinolin-4-yl)propyl]-1-[2-(cyclohexylthio)ethyl]piperidine-3-acetic acid (3RS,4RS) or (3SR,4RS)-4-[3-(R,S)-fluoro-3-(3-fluoro-6-methoxyquinolin-4-yl)propyl]-1-[2-(thien-2-yl)thioethyl]piperidine-3-acetic acid (3RS,4RS) or (3SR,4RS)-4-[3-(R,S)-fluoro-3-(3-fluoro-6-methoxyquinolin-4-yl)propyl]-1-[2-(1,3-thiazol-2-yl)thioethyl]piperidine-3-acetic acid (3RS,4RS) or (3SR,4RS)-4-[3-(R,S)-fluoro-3-(3-fluoro-6-methoxyquinolin-4-yl)propyl]-1-[2-(pyridin-2-yl)thioethyl]piperidine-3-acetic acid (3RS,4RS) or (3SR,4RS)-4-[3-(R,S)-fluoro-3-(3-fluoro-6-methoxyquinolin-4-yl)propyl]-1-[3-(3,5-difluorophenyl)prop-2-ynyl]piperidine-3-acetic acid (3RS,4RS) or (3SR,4RS)-4-[3-(R,S)-fluoro-3-(3-fluoro-6-methoxyquinolin-4-yl)propyl]-1-[3-(2,3,5-trifluorophenyl)prop-2-ynyl]piperidine-3-acetic acid (3RS,4RS) or (3SR,4RS)-4-[3-(R,S)-fluoro-3-(3-fluoro-6-methoxyquinolin-4-yl)propyl]-1-[3-(thien-2-yl)prop-2-ynyl]piperidine-3-acetic acid (3RS,4RS) or (3SR,4RS)-4-[3-(R,S)-amino-3-(3-fluoro-6-methoxyquinolin-4-yl)propyl]-1-(2-phenylthioethyl)piperidine-3-acetic acid (3RS,4RS) or (3SR,4RS)-4-[3-(R,S)-amino-3-(3-fluoro-6-methoxyquinolin-4-yl)propyl]-1-[2-(3-fluorophenylthio)ethyl]piperidine-3-acetic acid (3RS,4RS) or (3SR,4RS)-4-[3-(R,S)-amino-3-(3-fluoro-6-methoxyquinolin-4-yl)propyl]-1-[2-(3,5-difluorophenylthio)ethyl]piperidine-3-acetic acid (3RS,4RS) or (3SR,4RS)-4-[3-(R,S)-amino-3-(3-fluoro-6-methoxyquinolin-4-yl)propyl]-1-[2-(2,3,5-trifluorophenylthio)ethyl]piperidine-3-acetic acid (3RS,4RS) or (3SR,4RS)-4-[3-(R,S)-amino-3-(3-fluoro-6-methoxyquinolin-4-yl)propyl]-1-[3-(n-propylthio)propyl]piperidine-3-acetic acid (3RS,4RS) or (3SR,4RS)-4-[3-(R,S) amino-3-(3-fluoro-6-methoxyquinolin-4-yl)propyl]-1-[2-(n-butylthio)ethyl]piperidine-3-acetic acid (3RS,4RS) or (3SR,4RS)-4-[3-(R,S)-amino-3-(3-fluoro-6-methoxyquinolin-4-yl)propyl]-1-[2-(cyclopropylthio)ethyl]piperidine-3-acetic acid (3RS,4RS) or (3SR,4RS)-4-[3-(R,S)-amino-3-(3-fluoro-6-methoxyquinolin-4-yl)propyl]-1-[2-(cyclobutylthio)ethyl]piperidine-3-acetic acid (3RS,4RS) or (3SR,4RS)-4-[3-(R,S)-amino-3-(3-fluoro-6-methoxyquinolin-4-yl)propyl]-1-[2-(cyclopentylthio)ethyl]piperidine-3-acetic acid (3RS,4RS) or (3SR,4RS)-4-[3-(R,S)-amino-3-(3-fluoro-6-methoxyquinolin-4-yl)propyl-1-[2-(cyclohexylthio)ethyl]piperidine-3-acetic acid (3RS,4RS) or (3SR,4RS)-4-[3-(R,S)-amino-3-(3-fluoro-6-methoxyquinolin-4-yl)propyl]-1-[2-(5-fluoro-thien-2-yl)thioethyl]piperidine-3-acetic acid (3RS,4RS) or (3SR,4RS)-4-[3-(R,S)-amino-3-(3-fluoro-6-methoxyquinolin-4-yl)propyl]-1-[2-(thien-3-yl)thioethyl]piperidine-3-acetic acid (3RS,4RS) or (3SR,4RS)-4-[3-(R,S)-amino-3-(3-fluoro-6-methoxyquinolin-4-yl)propyl]-1-[2-(1,3-thiazol-2-yl)thioethyl]piperidine-3-acetic acid (3RS,4RS) or (3SR,4RS)-4-[3-(R,S)-amino-3-(3-fluoro-6-methoxyquinolin-4-yl)propyl]-1-[2-(pyridin-2-yl)thioethyl]piperidine-3-acetic acid (3RS,4RS) or (3SR,4RS)-4-[3-(R,S)-amino-3-(3-fluoro-6-methoxyquinolin-4-yl)propyl]-1-[2-(3-fluoropyridin-2-yl)thioethyl]piperidine-3-acetic acid (3RS,4RS) or (3SR,4RS)-4-[3-(R,S)-amino-3-(3-fluoro-6-methoxyquinolin-4-yl)propyl]-1-[3-(3-fluorophenyl)prop-2-ynyl]piperidine-3-acetic acid (3RS,4RS) or (3SR,4RS)-4-[3-(R,S)-amino-3-(3-fluoro-6-methoxyquinolin-4-yl)propyl]-1-[3-(2,5-difluorophenyl)prop-2-ynyl]piperidine-3-acetic acid (3RS,4RS) or (3SR,4RS)-4-[3-(R,S)-amino-3-(3-fluoro-6-methoxyquinolin-4-yl)propyl]-1-[3-(3,5-difluorophenyl)prop-2-ynyl]piperidine-3-acetic acid (3RS,4RS) or (3SR,4RS)-4-[3-(R,S)-amino-3-(3-fluoro-6-methoxyquinolin-4-yl)propyl]-1-[3-(2,3,5-trifluorophenyl)prop-2-ynyl]piperidine-3-acetic acid (3RS,4RS) or (3SR,4RS)-4-[3-(R,S)-amino-3-(3-fluoro-6-methoxyquinolin-4-yl)propyl]-1-[3-(thien-2-yl)prop-2-ynyl]piperidine-3-acetic acid (3RS,4RS) or (3SR,4RS)-4-[3-(R,S)-amino-3-(3-fluoro-6-methoxyquinolin-4-yl)propyl]-1-[3-(thien-3-yl)prop-2-ynyl]piperidine-3-acetic acid as well as their salts.

The following examples illustrate the present invention but do not limit it.

EXAMPLE 1 a) (3RS,4RS)-4-[3-(3-Fluoro-6-methoxyquinolin-4-yl)-propyl]-1-[2-(thien-2-yl)thioethyl]Piperidine-3-acetic Acid Dihydrochloride A solution of 480 mg of methyl (3RS,4RS)-4-[3-(3-fluoro-6-methoxyquinolin-4-yl)propyl]-1-[2-(thien-2-yl) thioethyl]piperidine-3-acetate, 5 cm³ of dioxane and 2.25 cm³ of a 1 N aqueous sodium hydroxide solution was heated, with stirring, at a temperature in the region of 60° C. for 1 hour 30 minutes. After concentrating the reaction mixture under reduced pressure (5 kPa) at a temperature the region of 40° C., the residue obtained was taken up in 50 cm³ of water and 20 cm³ of ether. The aqueous phase was separated after settling out and then washed twice with 10 cm³ of ether, it was then acidified by pouring 2.25 cm³ of 1 N hydrochloric acid. The precipitate formed was dissolved by adding 75 cm³ of dichloromethane. The organic phase was separated after settling out, dried over magnesium sulfate, filtered, and then concentrated under reduced pressure (5 kPa) at a temperature in the region of 40° C. The product obtained was then stirred in 30 cm³ of acetone. 4 cm³ of 4 N hydrochloric acid in dioxane were then poured over this solution. The reaction mixture was concentrated under reduced pressure (5 kPa) at a temperature in the region of 40° C. and then 15 cm³ of acetone were added. This operation was repeated 5 times until a yellow solid was obtained, which solid was drained and then dried in a desiccator under reduced pressure (10 Pa) at a temperature of about 45° C. 395 mg of (3RS,4RS)-4-[3-(3-fluoro-6-methoxyquinolin-4-yl)-propyl]-1-[2-(thien-2-yl)thioethyl] piperidine-3-acetic acid dihydrochloride were obtained in the form of a solid, which was off-white in color.

¹H NMR spectrum (400 MHz, (CD₃)₂SO d6 at a temperature of 393K, δ in ppm): from 1.40 to 1.90 (mt: 7H); 2.29 (dd, J=16 and 5.5 Hz: 1H); 2.46 (unresolved complex: 1H); from 2.65 to 3.45 (mt: 5H); 3.09 (broad t, J=7.5 Hz: 2H); 3.23 (broad s: 4H); 3.99 (s: 3H); 7.09 (dd, J=5.5 and 3.5 Hz: 1H); 7.27 (dd, J=3.5 and 1.5 Hz: 1H); 7.38 (d, J=3 Hz: 1H); 7.40 (dd, J=9 and 3 Hz: 1H); 7.62 (dd, J=5.5 and 1.5 Hz: 1H); 7.98 (d, J=9 Hz: 1H); 8.64 (broad s: 1H).

b) Methyl (3RS,4RS)-4-[3-(3-fluoro-6-methoxyquinolin-4-yl)propyl]-1-[2-(2-thienylthio)ethyl]piperidine-3-acetate A suspension composed of 0.95 g of methyl (3RS,4RS) and (3SR,4RS)-4-[3-(3-fluoro-6-methoxy-quinolin-4-yl) propyl]piperidine-3-acetate, 0.7 g of potassium carbonate, 0.68 g of 2-(2-bromoethylthio)-thiophene in 40 cm³ of dimethylformamide was stirred for 16 hours at a temperature in the region of 60° C. under an inert atmosphere. After cooling to about 20° C., the reaction mixture was poured over 200 cm³ of water and 200 cm³ of ethyl acetate. The organic phase was separated after settling out and then washed 5 times with 100 cm³ of water and then with 100 cm³ of a saturated aqueous sodium chloride solution, dried over magnesium sulfate, filtered, and then concentrated under reduced pressure (5 kPa) at a temperature in the region of 40° C. The evaporation residue obtained was purified by chromatography, under a nitrogen pressure of 50 kPa, on a column of silica gel (particle size 20–45 μ; diameter 2 cm; height 40 cm), eluting with a cyclohexane-ethyl acetate (68/32 by volume) mixture. 15-cm³ fractions were collected. Fractions 15 to 21 were concentrated. 480 mg of methyl (3RS,4RS)-4-[3-(3-fluoro-6-methoxyquinolin-4-yl)propyl]-1-[2-(thien-2-yl)thioethyl]piperidine-3-acetate were obtained in the form of an orange-colored oil.

¹H NMR spectrum (300 MHz, (CD₃)₂SO d6, δ in ppm): from 1.15 to 1.70 (mt: 7H); from 1.90 to 2.05 (mt: 2H); 2.08 (unresolved complex: 1H); 2.17 (broad dd, J=16 and 4 Hz: 1H); from 2.35 to 2.80 (mt: 5H); 2.90 (mt: 2H); 3.07 (broad t, J=7.5 Hz: 2H); 3.57 (s: 3H); 3.97 (s: 3H); 7.06 (dd, J=5.5 and 4 Hz: 1 H); 7.17 (dd, J=4 and 1.5 Hz: 1H); 7.38 (d, J=3 Hz: 1H); 7.40 (dd, J=9 and 3 Hz: 1H); 7.62 (dd, J=5.5 and 1.5 Hz: 1H); 7.97 (d, J=9 Hz: 1H); 8.70 (broad s: 1H).

c) Methyl (3RS,4RS) and (3SR,4RS)-4-[3-(3-fluoro-6-methoxyquinolin-4-yl)propyl]piperidine-3-acetate 2.65 g of methyl (4RS)-1-benzyloxycarbonyl-4-[3-(3-fluoro-6-methoxyquinolin-4-yl)propyl]piperidine-3-ylideneacetate, Z isomer, 45 cm³ of absolute ethanol and 265 mg of 10% palladium on carbon were introduced into an autoclave. The reaction mixture was stirred under 5 bar of hydrogen at 22° C. for 24 hours and then filtered on supercel, and rinsed 5 times with 20 cm³ of absolute ethanol. The combined filtrates were concentrated under reduced pressure (5 kPa) at a temperature in the region of 40° C. 1.85 g of methyl (3RS,4RS) and (3SR,4RS)-4-[3-(3-fluoro-6-methoxy-quinolin-4-yl)propyl]piperidine-3-acetate were obtained in the form of a colorless oil.

¹H NMR spectrum (300 MHz, (CD₃)₂SO d6, δ in ppm): from 1.10 to 1.80 (mt: 7H); from 1.90 to 2.30 (mt: 2H); from 2.35 to 2.60 (mt: 3H); from 2.65 to 2.95 (mt: 2H); 3.06 (mt: 2H); 3.55 and 3.56 (2s: 3H in total); 3.95 to 3.96 (2s: 3H in total); from 7.30 to 7.45 (mt: 2H); 7.96 (d, J=9 Hz: 1H); 8.70 (broad s: 1H).

d) Methyl (4RS)-1-benzyloxycarbonyl-4-[3-(3-fluoro-6-methoxyquinolin-4-yl)propyl]piperidine-3-ylidenacetate, Z Isomer A solution of 5.8 g of methyl (4RS)-4-allyl-1-benzyloxycarbonylpiperidin-3-ylideneacetate (Z isomer) in 15 cm³ of tetrahydrofuran was slowly added, at a temperature in the region of 0° C., with stirring and under an inert atmosphere, to 45 cm³ of a 0.5 M 9-borabicyclo[3.3.1] nonane solution in tetrahydrofuran. The mixture was then brought to a temperature in the region of 20° C. while the stirring was continued for a further 4 hours. 5.5 g of 4-iodo-3-fluoro-6-methoxyquinoline in solution in 100 cm³ of tetrahydrofuran were added, followed by 11.2 g of tribasic potassium phosphate, and finally 386 mg of palladiumdiphenylphosphinoferrocene chloride. The reaction mixture was heated for 2 hours under reflux and then stirred for 48 hours at room temperature. The suspension obtained was filtered. The filtrate was concentrated and then taken up in 200 cm³ of ethyl acetate. The solution obtained was washed twice with 200 cm³ of water and then twice with 200 cm³ of a saturated aqueous sodium chloride solution, dried over magnesium sulfate, filtered and then concentrated under reduced pressure (5 kPa) at a temperature in the region of 40° C. 15 g of an oil were obtained, which oil was purified by chromatography, under a nitrogen pressure of 50 kPa, on a column of silica gel (particle size 20–45μ; diameter 6 cm; height 38 cm), eluting with a cyclohexane-ethyl acetate mixture (85/15 by volume, making a gradient up to 70/30 by volume). 200-cm³ fractions were collected. Fractions 31 to 34 were combined and then concentrated. 4.7 g of methyl (4RS)-1-benzyloxycarbonyl-4-[3-(3-fluoro-6-methoxyquinolin-4-yl)propyl]piperidine-3-ylidenacetate (Z isomer) were obtained in the form of a colorless oil.

Infrared spectrum (CCl₄): 3091; 3068; 3034; 1705; 1655; 1622; 1507; 1468; 1434; 1361; 1263; 1231; 1207; 1173; 1141; 1034; 909; 832 and 696 cm¹ e) Methyl (4RS)-4-allyl-1-benzyloxycarbonylpiperidin-3-ylidenacetate, Z Isomer

A solution containing 16.3 g of (4RS)-4-allyl-1-benzyloxycarbonylpiperidin-3-one in 200 cm³ of toluene was stirred under reflux with methyl (triphenylphosphoranylidene)acetate, under an inert atmosphere, for 16 hours. After cooling to about 20° C., the reaction mixture was concentrated under reduced pressure (5 kPa) at a temperature in the region of 40° C., the residue obtained, solubilized in 50 cm³ of dichloromethane in the hot state, was purified by chromatography, under a nitrogen pressure of 50 kPa, on a column of silica gel (particle size 20–45μ; diameter 10 cm; height 45 cm), eluting with a cyclohexane-ethyl acetate (80/20 by volume) mixture. 250-cm³ fractions were collected. Fractions 13 to 15 were combined and then concentrated as above. 5.8 g of methyl (4RS)-4-allyl-1-benzyloxycarbonylpiperidin-3-ylidenacetate (Z isomer) were obtained in the form of a colorless oil.

Infrared spectrum (CCl₄): 3068; 3034; 2949; 2853; 1722; 1705; 1655; 1643; 1434; 1260; 1200; 1174; 1144; 993; 918 and 696 cm⁻¹

(4RS)-4-allyl-1benzyloxycarbonylpiperidin-3-one may be prepared according to Takeuchi Y et al. described in Synthesis, 10:1814 (1999).

EXAMPLE 2 a) (3RS,4RS)-4-[3-(R,S)-hydroxy-3-(3-fluoro-6-methoxyquinolin-4-yl)propyl]-1-[2-(thien-2-ylthio)ethyl] piperidine-3-acetic Acid Dihydrochloride A solution of 70 mg of ethyl (3RS,4RS)-4-[3-(R,S)-hydroxy-3-(3-fluoro-6-methoxyquinolin-4-yl)propyl]-1-[2-(thien-2-ylthio)ethyl]piperidine-3-acetate, 1 cm³ of dioxane and 0.3 cm³ of a 1 N aqueous sodium hydroxide solution was heated, with stirring, at a temperature in the region of 60° C. for 1 hour. After concentrating the reaction mixture under reduced pressure (5 kPa) at a temperature in the region of 40° C., the residue obtained was taken up in 25 cm³ of water and 10 cm³ of dichloromethane. The aqueous phase was separated after settling out and then acidified by pouring 0.3 cm³ of 1 N hydrochloric acid. The precipitate formed was dissolved by adding 25 cm³ of dichloromethane. The organic phase was washed with 10 cm³ of a saturated aqueous sodium chloride solution and dried over magnesium sulfate, filtered and concentrated under reduced pressure (5 kPa) at a temperature in the region of 40° C. The residue obtained was then dissolved in the hot state in 2 cm³ of acetone. 0.07 cm³ of 4 N hydrochloric acid in dioxane were poured over this solution. The resulting mixture was concentrated under reduced pressure (5 kPa) at a temperature in the region of 40° C. 72 mg of (3RS,4RS)-4-[3-(R,S)-hydroxy-3-(3-fluoro-6-methoxy quinolin-4-yl)propyl]-1-[2-(thien-2-ylthio)ethyl]piperidine-3 acetic acid dihydrochloride were obtained in the form of a powder, which was white in color.

¹H NMR spectrum (400 MHz, (CD₃)₂SO d6 with a few drops of CD3COOD d4 at a temperature of 373K, δ in ppm): from 1.20 to 2.00 (mt: 7H); from 2.00 to 2.60 (mt: 5H); from 2.75 to 3.20 (mt: 6H); 3.94 (s: 3H); 4.89 (broad t, J=7 Hz: 1H); 7.07 (mt: 1H); 7.24 (mt: 1H); 7.37 (dd, J=9 and 2.5 Hz: 1H); 7.60 (broad d, J=5 Hz: 1H); from 7.90 to 8.00 (mt: 2H); 8.62 (broad s: 1H).

b) Methyl (3RS,4RS)-4-[3-(R,S)-hydroxy-3-(3-fluoro-6-methoxyquinolin-4-yl)propyl]-1-[2-(2-thienylthio)ethyl] piperidine-3-acetate A solution composed of 0.92 g of methyl (3RS,4RS) and (3SR,4RS)-4-[3-(R,S)-hydroxy-3-(3-fluoro-6-methoxyquinolin-4-yl)propyl]piperidine-3-acetate dihydrochloride, 0.85 cm³ of triethylamine, 535 mg of 2-(2-bromoethylthio)thiophene in 30 cm³ of anhydrous dimethylformamide was stirred for 4 hours 30 minutes at a temperature in the region of 60° C. under an inert atmosphere. 0.3 cm³ of triethylamine were then added and the mixture was again heated at 60° C. under an inert atmosphere for 15 hours. After cooling to about 20° C., the reaction mixture was poured over 100 cm³ of water and 100 cm³ of ethyl acetate. The organic phase was separated after settling out, washed 4 times with 15 cm³ of water and then twice with 50 cm³ of a saturated aqueous sodium chloride solution, dried over magnesium sulfate, filtered and concentrated under reduced pressure (5 kPa) at a temperature in the region of 40° C. The residues obtained was purified by chromatography, under a nitrogen pressure of 50 kPa, on a column of silica gel (particle size 20–45μ; diameter 1 cm; height 40 cm), eluting with a cyclohexane-ethyl acetate (50/50 by volume) mixture. 20-cm³ fractions were collected. Fractions 13 to 15 were concentrated. 70 mg of methyl (3RS,4RS)-4-[3-(R,S)-hydroxy-3-(3-fluoro-6-methoxyquinolin-4-yl)-3-(R,S)-hydroxypropyl]-1-[2-(2-thienylthio)ethyl]piperidine-3-acetate were obtained in the form of an oil, which was yellow in color.

Infrared spectrum (CCl₄): 3617; 2934; 2799; 2764; 1737; 1623; 1508; 1467; 1231; 1033; 1011; 834 and 698 cm⁻¹ c) Methyl (3RS,4RS) and (3SR,4RS)-4-[3-(R,S)-hydroxy-3-(3-fluoro-6-methoxyquinolin-4-yl)propyl]piperidine-3-acetate Dihydrochloride A solution of 940 mg of (3RS,4RS) and (3SR,4RS)-4-[3-(R,S)-hydroxy-3-(3-fluoro-6-methoxyquinolin-4-yl) propyl]-1-(tert-butyloxycarbonyl)piperidine-3-acetic acid in 20 cm³ of methanol was cooled to a temperature in the region of −25° C., with stirring and under an inert atmosphere. 0.43 cm³ of thionyl chloride were added to this solution over 5 minutes. The mixture was brought to a temperature in the region of 20° C. while the stirring was continued for a further 1 hour 30 minutes. The reaction mixture was concentrated under reduced pressure (5 kPa) at a temperature in the region of 40° C. and then 30 cm³ of methanol were added. This series of operations was repeated 3 times. 920 mg of methyl (3RS,4RS) and (3SR,4RS)-4-[3-(R,S)-hydroxy-3-(3-fluoro-6-methoxyquinolin-4-yl)propyl] piperidine-3-acetate dihydrochloride were obtained in the form of a yellow foam.

Infrared spectrum (KBr): 3249; 1949; 2503; 2020; 1731; 1622; 1604; 1555; 1497; 1457; 1420; 1308; 1242; 1200; 1175; 1080; 1014; 872; 832 and 795 cm⁻¹ d) (3RS,4RS) and (3SR,4RS)-4-[3-(R,S)-hydroxy-3-(3-fluoro-6-methoxyquinolin-4-yl)propyl]-1-(tert-butyloxycarbonyl)piperidine-3-acetic Acid A solution of 1.16 g of methyl (3RS,4RS) and (3SR,4RS)-4-[3-(3-fluoro-6-methoxyquinolin-4-yl)₃-propyl]-1-(tert-butyloxycarbonyl)piperidine-3-acetate, 100 cm³ of anhydrous dimethyl sulfoxide and 25 cm³ of anhydrous tert-butanol was stirred under an inert atmosphere free of water at 20° C. This colorless solution was purged with pure oxygen until the reaction mixture became saturated. A solution containing 685 mg of potassium tert-butoxide in 8 cm³ of anhydrous tert-butanol was then added. Oxygen was again introduced by bubbling for a further 3 hours and 30 minutes with vigorous stirring. The yellow solution obtained was purged with nitrogen and then cooled to 0° C. 0.5 cm³ of pure acetic acid in 20 cm³ of water were then added followed by 200 cm³ of ether. The organic phase was separated after settling out, washed 7 times with 20 cm³ of water and 3 times with 20 cm³ of a saturated aqueous sodium chloride solution, dried over magnesium sulfate, filtered and concentrated under reduced pressure (5 kPa) at a temperature in the region of 40° C. A gum was obtained, which was taken up in 20 cm³ of ether. The medium was again concentrated under the same conditions as above. 945 mg of (3RS,4RS) and (3SR,4RS)-4-[3-(R,S)-hydroxy-3-(3-fluoro-6-methoxyquinolin-4-yl)propyl]-1-(tert-butyloxycarbonyl)piperidine-3-acetic acid were obtained in the form of a white foam.

Infrared spectrum (KBr): 2973; 2932; 2864; 1693; 1668; 1623; 1510; 1468; 1429; 1366; 1232; 1166; 1030 and 831 cm$^{-1}$ Infrared spectrum (CH$_2$Cl$_2$): 3600; 2982; 2939; 2867; 1710; 1682; 1623; 1509; 1468; 1429; 1367; 1231; 1162; 1030; 909; 896 and 834 cm$^{-1}$ e) Methyl (3RS,4RS) and (3SR,4RS)-[3-(3fluoro-6-methoxyquinolin-4-yl)-3-propyl]-1-(tert-butyloxycarbonyl)piperidine-3-acetate A solution of 1.85 g of methyl (3RS,4RS) and (3SR,4RS)-4-[3-(3-fluoro-6-methoxyquinolin-4-yl)propyl]piperidine-3-acetate, 0.7 cm$^3$ of triethylamine and 40 cm$^3$ of dichloromethane was cooled, to a temperature in the region of 0° C., with stirring and under an argon atmosphere. A solution of 1.16 g of di-tert-butyldicarbonate dissolved in 40 cm$^3$ of dichloromethane was added to this colorless solution over 20 minutes. The mixture was brought to a temperature in the region of 20° C. while the stirring was continued for a further 10 hours. 200 cm$^3$ of water were then added to the reaction mixture. The organic phase was separated after settling out, washed with 100 cm$^3$ of a saturated aqueous sodium chloride solution, dried over magnesium sulfate, filtered and then concentrated under reduced pressure (5 kPa) at a temperature in the region of 40° C. An oil was obtained, which was purified by chromatography, under a nitrogen pressure of 50 kPa, on a column of silica gel (particle size 20–45µ; diameter 2 cm; height 20 cm), eluting with a cyclohexane-ethyl acetate (70/30 by volume) mixture. 40-cm$^3$ fractions were collected. Fractions 8 to 12 were combined and then concentrated as above. 2.16 g of methyl (3RS,4RS) and (3SR,4RS)-4-[3-(3-fluoro-6-methoxyquinolin-4-yl)-3-propyl]-1-(tert-butyloxycarbonyl)piperidine-3-acetate were obtained in the form of a colorless oil.

Infrared spectrum (CCl$_4$) 3006; 1740; 1695; 1622; 1507; 1468; 1428; 1366; 1231; 1166; 1034; 909 and 832 cm$^-$

EXAMPLE 3 a) (3S,4RS)-4-[3-(3-fluoro-6-methoxyquinolin-4-yl)propyl]-1-[2-(2-thienylthio)ethyl]piperidine-3-acetic Acid Hydrochloride A solution of 195 mg of methyl (3SR,4RS)-4-[3-(3-fluoro-6-methoxyquinolin-4-yl)propyl]-1-[2-(2-thienylthio)ethyl]piperidine-3-acetate, 2 cm$^3$ of dioxane and 0.9 cm$^3$ of a 1 N aqueous sodium hydroxide solution was heated, with stirring, at a temperature in the region of 60° C. for 1 hour. After concentrating the reaction mixture under reduced pressure (5 kPa) at a temperature in the region of 40° C., the residue obtained was taken up in 20 cm$^3$ of water and 10 cm$^3$ of ether. The aqueous phase was separated after settling out and then acidified by adding 0.9 cm$^3$ of 1 N hydrochloric acid. The precipitate formed was dissolved with 20 cm$^3$ of dichloromethane. The organic phase was washed twice with 10 cm$^3$ of a saturated aqueous sodium chloride solution, dried over magnesium sulfate, filtered, concentrated under reduced pressure (5 kPa) at a temperature in the region of 40° C. The product obtained was then stirred in 20 cm$^3$ of acetone. A solution of 2 cm$^3$ of 4 N hydrochloric acid in dioxane was poured over this solution. The reaction mixture was concentrated under reduced pressure (5 kPa) at a temperature in the region of 40° C. and then 5 cm$^3$ of acetone were added. This operation was repeated 4 times. 155 mg of (3SR,4RS)-4-[3-(3-fluoro-6-methoxyquinolin-4-yl)propyl]-1-[2-(2-thienylthio)ethyl]piperidine-3-acetic acid hydrochloride were obtained in the form of a solid which was off-white in color.

$^1$H NMR spectrum (300 MHz, (CD$_3$)$_2$SO d6, δ in ppm): from 1.15 to 2.10 (mt: 8H); 2.10 (dd, J=15 and 7.5 Hz: 1H); 2.47 (dd, J=15 and 4 Hz: 1H); from 2.70 to 2.95 (mt: 2H); 3.07 (broad t, J=7 Hz: 2H); 3.20 (mt: 4H); 3.44 (mt: 2H); 3.96 (s: 3H); 7.11 (dd, J=5.5 and 4 Hz: 1H); 7.32 (dd, J=4 and 1.5 Hz: 1H); 7.40 (mt: 1H); 7.41 (dd, J=9 and 2.5 Hz: 1H); 7.72 (dd, J=5.5 and 1.5 Hz: 1H); 7.97 (d, J=9 Hz: 1H); 8.71 (broad s: 1H); from 9.85 to 10.05 (unresolved complex: 1H).

b) Methyl (3SR,4RS)-[3-(3-fluoro-6-methoxyquinolin-4-yl)propyl]-1-[2-(2-thienylthio)ethyl]piperidine-3-acetate A solution composed of 0.95 g of methyl (3RS,4RS) and (3SR,4RS)-4-[3-(3-fluoro-6-methoxyquinolin-4-yl)propyl]piperidine-3-acetate, 0.7 g of potassium carbonate, 0.68 g of 2-(2-bromoethylthio)thiophene in 40 cm$^3$ of dimethylformamide was stirred for 16 hours at a temperature in the region of 60° C. under an inert atmosphere. After cooling to about 20° C., the reaction mixture was supplemented with 200 cm$^3$ of water and 200 cm$^3$ of ethyl acetate. The organic phase was separated after settling out and then washed 5 times with 100 cm$^3$ of water and then with 100 cm$^3$ of a saturated aqueous sodium chloride solution, dried over magnesium sulfate, filtered and concentrated under reduced pressure (5 kPa) at a temperature in the region of 40° C. The evaporation residue obtained was purified by chromatography, under a nitrogen pressure of 50 kPa, on a column of silica gel (particle size 20–45µ; diameter 2 cm; height 40 cm), eluting with a cyclohexane-ethyl acetate (68/32 by volume) mixture. 15-cm$^3$ fractions were collected. Fractions 33 to 36 were concentrated. 195 mg of methyl (3SR,4RS)-4-[3-(3-fluoro-6-methoxyquinolin-4-yl)propyl]-1-[2-(2-thienylthio)ethyl]piperidine-3-acetate were obtained in the form of an orange-colored oil.

$^1$H NMR spectrum (300 MHz, (CD$_3$)$_2$SO d6, δ in ppm): from 1.00 to 1.80 (mt: 9H); 1.89 (very broad t, J=105 Hz: 1H); 2.07 (dd, J=15 and 7.5 Hz: 1H); from 2.35 to 2.55 (mt: 3H); from 2.65 to 2.80 (mt: 2H); 2.90 (t, J=7 Hz: 2H); 3.05 (broad t, J=6.5 Hz: 2H); 3.56 (s: 3H); 3.95 (s: 3H); 7.04 (dd, J=5 and 3.5 Hz: 1H); 7.17 (dd, J=3.5 and 1.5 Hz: 1H); 7.37 (mt: 1H); 7.40 (dd, J=9 and 2.5 Hz: 1H); 7.60 (dd, J=5 and 1.5 Hz: 1H); 7.96 (d, J=9 Hz: 1H); 8.69 (broad s: 1H).

EXAMPLE 4 a) (3RS,4RS)-4-[3-(R,S)-amino-3-(3-fluoro-6-methoxyquinolin-4-yl)propyl]-1-[2-(2-thienylthio)ethyl]piperidine-3-acetic Acid A mixture of 0.355 g of methyl (3RS,4RS)-4-[3-(R,S)-amino-3-(3-fluoro-6-methoxyquinolin-4-yl)propyl]-1-[2-(2-thienylthio)ethyl]piperidine-3-acetate in 1.66-cm$^3$ of a 1 N aqueous sodium hydroxide solution and 5-cm$^3$ of dioxane was heated at a temperature in the region of 60° C., with stirring, for 2 hours. After cooling to about 20° C., the reaction mixture was concentrated to dryness under reduced pressure (2 kPa) at a temperature in the region of 50° C. The evaporation residue obtained was taken up in 30-cm$^3$ of water and 30-cm$^3$ of diethyl ether, the aqueous phase was separated after settling out and neutralized with 1.66-cm$^3$ of a 1 N aqueous hydrochloric acid solution and was then extracted twice with 100-cm$^3$ of ethyl acetate. The organic phase was dried over magnesium sulfate, filtered and then concentrated to dryness according to the same conditions above. 0.238 g of (3RS,4RS)-4-[3-(R,S)-amino-3-(3-fluoro-6-methoxyquinolin-4-yl)propyl]-1-[2-(2-thienylthio)ethyl]piperidine-3-acetic acid were obtained in the form of a white solid.

$^1$H NMR spectrum (300 MHz, (CD$_3$)$_2$SO d6, δ in ppm): from 0.95 to 2.80 (mts: 16H); 2.87 (mt: 2H); 3.93 (s: 3H); 4.65 (broad t, J=7 Hz: 1H); 7.04 (broad dd, J=5.5 and 3.5 Hz:

1H); 7.16 (broad d, J=3.5 Hz: 1H); 7.37 (very broad d, J=9.5 Hz: 1H); 7.60 (broad d, J=5.5 Hz: 1H); 7.85 (mt: 1H); 7.94 (d, J=9.5 Hz: 1H); 8.66 (mt: 1H).

b) Methyl (3RS,4RS)A-[3-(R,S)-amino-3-(3-fluoro-6-methoxyquinolin-4-yl)propyl]-1-[2-(2-thienylthio)ethyl]piperidine-3-acetate 0.695 g of sodium borohydride was added in several portions to a mixture of 0.98 g of methyl (3RS,4RS)-4-[3-hydroxyimino-3-(3-fluoro-6-methoxyquinolin-4-yl)propyl]-1-[2-(2-thienylthio)ethyl]piperidine-3-acetate in 50-cm$^3$ of methanol cooled to the region of −5° C., with stirring and under inert atmosphere. The reaction was very exothermic and in the vicinity of 0° C., 0.365 g of molybdenum trioxide were added all at once. The reaction mixture was stirred in the region of 20° C. for 20 hours and then it was cooled to the vicinity of −6° C. and 0.695 g of sodium borohydride and 0.365 g of molybdenum trioxide were again added. The reaction mixture was stirred for 5 hours in the region of 20° C. and was then filtered on celite and the insoluble matter was washed twice with 50-cm$^3$ of methanol. The filtrate was concentrated to dryness under reduced pressure (2 kPa) at a temperature in the region of 40° C. The evaporation residue was purified by chromatography under an argon pressure of 50 kPa, on a column of silica gel (particle size 40–60 m; diameter 3 cm; height 25 cm), eluting with a successive mixture of cyclohexane-ethyl acetate (50/50 by volume), ethyl acetate and then dichloromethane-methanol (90/10 by volume) and collecting 50-cm$^3$ fractions. Fractions 17 to 20 were combined and then concentrated to dryness according to the conditions described above. 0.355 g of methyl (3RS,4RS)-4-[3-(R,S)amino-3-(3-fluoro-6-methoxyquinolin-4-yl)propyl]-1-[2-(2-thienylthio)ethyl]piperidine-3-acetate were obtained in the form of a colorless oil.

Infrared spectrum: (CCl$_4$) 2932; 2765; 1736; 1623; 1508; 1230; 1167; 1033; 833 and 699 cm$^{-1}$ c) Methyl (3RS,4RS)-4-[3-hydroxyimino-3-(3-fluoro-6-methoxyquinolin-4-yl)propyl]-1-[2-(2-thienylthio)ethyl]piperidine-3-acetate 0.363 g of hydroxylamine hydrochloride was added in several portions to a mixture of 0.99 g of methyl (3RS,RS)-4-[3-oxo-3-(3-fluoro-6-methoxyquinolin-4-yl)propyl]-1-[2-(2-thienylthio)ethyl]piperidine-3-acetate in 10-cm$^3$ of pyridine, with stirring and under an inert atmosphere, and the resulting mixture was heated in the region of 60° C. for 16 hours. After cooling in the region of 20° C., the reaction mixture was concentrated to dryness under reduced pressure (8 kPa) at a temperature in the region of 55° C. The evaporation residue was taken up in 75-cm$^3$ of ethyl acetate and 40-cm$^3$ of distilled water. The organic phase was washed three times with 40-cm$^3$ of distilled water and 40-cm$^3$ of a saturated sodium chloride solution, dried over magnesium sulfate for 30 minutes, filtered and concentrated to dryness under reduced pressure (2 kPa) at a temperature in the region of 40° C. 0.98 g of methyl (3RS,4RS)-4-[3-hydroxyimino-3-(fluoro-6-methoxyquinolin-4-yl)propyl]-1-[2-(2-thienylthio)ethyl]piperidine-3-acetate were obtained in the form of a yellow gum.

| Mass spectrum: EI m/z = 528 | [M—OH]$^+$ | |
|---|---|---|
| m/z = 514 | [M—OCH$_3$]$^+$ | |
| m/z = 416 | [M—C$_5$H$_5$S$_2$]$^+$ | base peak |
| m/z = 115 | [C$_4$H$_3$S$_2$]$^+$ | |
| DCI m/z = 546 | MH$^+$ | | d) Methyl (3RS,4RS)-4-[3-oxo-3-(3-fluoro-6-methoxyquinolin-4-yl)propyl]-1-[2-(2-thienylthio)ethyl]piperidine-3-acetate 4.7-cm$^3$ of dimethyl sulfoxide in 15-cm$^3$ of dichloromethane were poured, over 10 minutes, into a solution of 3.3-cm$^3$ of oxalyl dichloride in 40 m$^3$ of dichloromethane cooled to −70° C., with stirring and under an inert atmosphere. After 10 minutes, a solution of 4 g of methyl (3RS,4RS)-4-[3-(R,S)-hydroxy-3-(3-fluoro-6-methoxyquinolin-4-yl)propyl]-1-[2-(2-thienylthio)ethyl]piperidine-3-acetate in 25-cm$^3$ of dichloromethane was poured in over 10 minutes. After 20 minutes, in the region of −70° C., 21-cm$^3$ of triethylamine in 20-cm$^3$ of dichloromethane were added dropwise over 15 minutes and the reaction mixture was stirred for 15 minutes in the region of −70° C. and then for 2 hours in the region of 20° C. 100-cm$^3$ of distilled water were poured over the reaction mixture, the organic phase was separated after settling out, washed with 100-cm$^3$ of a saturated aqueous sodium hydrogen carbonate solution, twice with 75-cm$^3$ of water and 75-cm$^3$ of a saturated aqueous sodium chloride solution. The organic extract was dried over magnesium sulfate for 30 minutes, filtered and concentrated to dryness under reduced pressure (2 kPa) at a temperature in the region of 40° C. The residue obtained was purified by chromatography under an argon pressure of 50 kPa, on a column of silica gel (particle size 40–60μ; diameter 3 cm; height 40 cm), eluting with a cyclohexane-ethyl acetate (60/40 by volume) mixture and collecting 50-cm$^3$ fractions. Fractions 11 to 16 were combined and then concentrated to dryness according to the conditions described above. 3.16 g of methyl (3RS,4RS)-4-[3-oxo-3-(fluoro-6-methoxyquinolin-4-yl)propyl]-1-[2-(2-thienylthio)ethyl]piperidine-3-acetate were obtained in the form of a yellow oil.

Infrared spectrum: (CCl$_4$): 2930;1738; 1699; 1621; 1505; 1231; 1198; 1154; 1028; 834; 699 cm$^{-1}$.

EXAMPLE 5 a) (3RS,4RS)-4-[3-(R,S)-hydroxy-3-(3-fluoro-6-methoxyquinolin-4-yl)propyl]-1-(2,5-difluorophenylthio)ethyl]piperidine-3-acetic Acid Hydrochloride A mixture of 0.2 g of methyl (3RS,4RS)-4-[3-(R,S)-hydroxy-3-(3-fluoro-6-methoxyquinolin-4-yl)propyl]-1-(2,5-difluorophenylthio)ethyl]piperidine-3-acetate in 3-cm$^3$ of methanol, 3-cm$^3$ of dioxane and 1.77-cm$^3$ of a 10 N aqueous sodium hydroxide solution was heated at a temperature in the region of 65° C., with stirring, for 22 hours. After cooling in the vicinity of 20° C., the reaction mixture was concentrated to dryness under reduced pressure (2 kPa) at a temperature in the region of 50° C. The evaporation residue obtained was taken up in 10-cm$^3$ of distilled water and acidified with a sufficient volume of a concentrated acetic acid solution in order to obtain a pH in the region of 5-6. The mixture was extracted with 20-cm$^3$ of ethyl acetate, the organic phase was dried over magnesium sulfate, filtered and concentrated to dryness according to the conditions described above. The oil obtained was taken up in 10-cm$^3$ of acetone and 10-cm$^3$ of a hydrochloric dioxane solution and then concentrated to dryness under reduced pressure (2 kPa) at a temperature in the region of 40° C. The residue was again taken up in 10-cm$^3$ of acetone and then concentrated to dryness under reduced pressure (2 kPa) at a temperature in the region of 40° C. and then dried in a desiccator for 18 hours. 0.181 g of (3RS,4RS)-4-[3-(R,S)-hydroxy-3-(3-fluoro-6-methoxyquinolin-4-yl)propyl]-1-(2,5-difluorophenylthio)ethyl]piperidine-3-acetic acid hydrochloride were obtained in the form of an orange-colored pourer solid melting in the vicinity of 124° C.

$^1$H NMR spectrum (300 MHz, (CD$_3$)$_2$SO d6, δ in ppm). A mixture of two stereoisomers in approximate proportions 60/40 was observed.

* from 1.00 to 3.85 (mts: 18H); 3.89 and 4.07 (2 broad s: 3H in total); 5.34 and 5.49 (2 mts: 1H in total); from 7.05 to 7.55 (mts: 4H); from 7.90 to 8.20 (mt: 2H); 8.68 and 8.85 (2 broad's: 1H in total); from 9.65 to 10.70 (unresolved complex: 2H in total).

b) Methyl (3RS,4RS)-4-[3-(R,S)-hydroxy-3-(3-fluoro-6-methoxyquinolin-4-yl)propyl]-1-[2-(2,5-difluorophenylthio)ethyl]piperidine-3-acetate A mixture of 6.5 g of methyl (3RS,4RS)-4-[3-(R,S)-hydroxy-3-(3-fluoro-6-methoxyquinolin-4-yl)propyl]piperidine-3-acetate dihydrochloride, 3.9 g of 2-(2-bromoethylthio)-1,4-difluorobenzene dissolved in 10-cm$^3$ of dimethylformamide, 2.32 g of potassium iodide, 5.8 g of potassium carbonate and 3.93-cm$^3$ of trietylamine in 200-cm$^3$ of acetonitrile was heated with stirring and under an inert atmosphere, for 22 hours at a temperature in the region of 70° C. After cooling to a temperature in the region of 20° C., the reaction mixture was filtered and the insoluble matter was washed twice with 30-cm$^3$ of acetonitrile. The filtrate was concentrated to dryness under reduced pressure (2 kPa) at a temperature in the region of 40° C. The evaporation residue was taken up in 100-cm$^3$ of distilled water and 150-cm$^3$ of ethyl acetate. The organic phase was washed 3 times with 100-cm$^3$ of distilled water and twice with 100-cm$^3$ of a saturated aqueous sodium chloride solution, dried over magnesium sulfate and concentrated to dryness according to the conditions described above. The oil obtained was purified by chromatography under an argon pressure of 50 kPa, on a column of silica gel (particle size 40–60 μm; diameter 4 cm), eluting with a cyclohexane-ethyl acetate (50/50 by volume) mixture and collecting 60-cm$^3$ fractions. The fractions containing the expected product were combined and then concentrated to dryness under reduced pressure (2 kPa) at a temperature in the region of 40° C. 1.7 g of methyl (3RS,4RS)-4-[3-(R,S)-hydroxy-3-(3-fluoro-6-methoxyquinolin-4-yl)propyl]-1-[2-(2,5-difluorophenylthio)ethyl]piperidine-3-acetate were obtained in the form of an orange-colored pourer viscous oil.

$^1$H NMR spectrum (300 MHz, (CD$_3$)$_2$SO d6, δ in ppm). The mixture of two stereoisomers in the proportions 50/50 was observed.

* from 0.90 to 2.60 (mt: 14H); from 2.60 to 2.80 (mt: 2H); 3.08 (broad t, J=7 Hz: 2H); 3.47 and 3.55 (2 s: 3H in total); 3.89 (s: 3H); 5.33 (very broad t, J=7 Hz: 1H); 5.83 (broad s: 1H); 7.05 (mt: 1H); from 7.15 to 7.35 (mt: 2H); 7.38 (d mt, J=9 Hz: 1H); from 7.90 to 8.00 (mt: 2H); 8.68 (broad s: 1H).

EXAMPLE 6 a) (3RS,4RS)-4-[3-(R,S)-amino-3-(3-fluoro-6-methoxyquinolin 4-yl)propyl]-1-[2-2,5-Difluorophenylthio) ethyl]piperidine-3-Acetic Acid Hydrochloride A mixture of 0.09 g of methyl (3RS,4RS)-4-[3-(R,S)-amino-3-(3-fluoro-6-methoxyquinolin-yl)propyl]-1-[2-(2,5-difluorophenylthio)ethyl]piperidine-3-acetate in 0.36-cm$^3$ of a 1 N aqueous sodium hydroxide solution and 3-cm$^3$ of dioxane was heated at a temperature in the region of 55° C., with stirring and under an inert atmosphere, for 4 hours. After cooling in the vicinity of 20° C., the reaction mixture was concentrated to dryness under reduced pressure (2 kPa) at a temperature in the region of 50° C. The evaporation residue obtained was taken up in 5-cm$^3$ of distilled water and acidified with a 1-N aqueous hydrochloric acid solution and was concentrated. The aqueous phase was washed with 8-cm$^3$ of dichloromethane and then concentrated according to the conditions described above. The residue obtained was taken up in 10-cm$^3$ of acetone and then it was filtered on sintered glass. 0.081 g of (3RS,4RS)-4-[3-(R,S)-amino-3-(3-fluoro-6-methoxyquinolin-4-yl)propyl]-1-[2-(2,5-difluorophenylthio)ethyl]piperidine-3-acetic acid hydrochloride were obtained in the form of a white solid.

NMR spectrum $^1$H NMR spectrum (400 MHz, (CD$_3$)$_2$SO d6 with addition of a few drops of CD$_3$COOD d4, at a temperature of 383K, δ in ppm). A mixture of stereoisomers was observed.

* from 1.20 to 2.55 (mt: 12H); from 2.80 to 3.60 (mt: 6H); 4.03 (s: 3H); 5.16 (mt: 1H); 7.12 (mt: 1H), 7.25 (mt: 1H); 7.42 (mt: 1H); 7.49 (broad d, J=9 Hz: 1H); 7.54 (mt: 1H); 8.06 (d, J=9 Hz: 1H); 8.76 (broad s: 1H).

b) Methyl (3RS,4RS)-4-[3-(R,S)-amino-3-(3-fluoro-6-methoxyquinolin-4yl)propyl]-1-[2-(2,5-difluorophenylthio) ethyl]piperidine-3-acetate 0.261 g of sodium borohydride was added, in several portions, to a mixture of 0.4 g of methyl (3RS,4RS)-4-[3-hydroxyimino-3-(3-fluoro-6-methoxyquinolin-4-yl)propyl]-1-[2-(2,5-difluorophenylthio)ethyl]piperidine-3-acetate in 25-cm$^3$ of methanol cooled in the region of −2° C., with stirring and under an inert atmosphere. The reaction mixture was stirred in the region of 0° C. for 20 minutes and then 0.14 g of molybdenum trioxide were added. The reaction mixture was stirred in the region of 20° C. for 24 hours and then it was cooled in the vicinity of −2° C. and 0.261 g of sodium borohydride and 0.14 g of molybdenum trioxide were again added. The reaction mixture was stirred for 18 hours in the region of 20° C. and then filtered on celite. The filtrate was concentrated to dryness under reduced pressure (2 kPa) at a temperature in the region of 40° C. The evaporation residue was purified by chromatography under an argon pressure of 50 kPa, on a column of silica gel (particle size 40–60 μm; diameter 3 cm), eluting with a successive mixture of cyclohexane-ethyl acetate (50/50 by volume) and then dichloromethane-methanol (90/10 by volume) and collecting 10-cm$^3$ fractions. Fractions 26 to 41 were combined and then concentrated to dryness according to the conditions described above. 0.202 g of methyl (3RS, 4RS)-4-[3-(R,S)-amino-3-(3-fluoro-6-methoxyquinolin-4-yl)propyl]-1-[2-(2,5-difluorophenylthio)ethyl]piperidine-3-acetate were obtained in the form of a colorless oil.

Infrared spectrum: (CCl$_4$)

2938; 1736; 1623; 1507; 1484; 1230; 1189; 1168; 1033; 909 and 833 cm$^{-1}$ c) Methyl (3RS,4RS)-4-[3-hydroxyimino-3-(3-fluoro-6-methoxyquinolin-4-yl)propyl]-1-[2-(2,5-difluorophenylthio)ethyl]piperidine-3-acetate 0.347 g of hydroxylamine hydrochloride were added, in several portions, to a mixture of 1 g of methyl (3RS,4RS)-4-[3-oxo-3-(3-fluoro-6-methoxyquinolin-4-yl)propyl]-1-[2-(2,5-difluorophenylthio)ethyl]piperidine-3-acetate in 10-cm$^3$ of pyridine, with stirring and under an inert atmosphere, and the resulting mixture was stirred in the region of 20° C. for 24 hours and then for 20 hours in the region of 50° C. and for 1.25 hours in the region of 62° C. After cooling in the region of 20° C., the reaction mixture was concentrated to dryness under reduced pressure (1.5 kPa) at a temperature in the region of 50° C. The evaporation residue was taken up in 70-cm$^3$ of ethyl acetate and 40-cm$^3$ of distilled water. The organic phase was separated after settling out, washed 3 times with 40-cm$^3$ of distilled water and 40-cm$^3$ of a saturated sodium chloride solution, dried over magnesium sulfate, filtered and concentrated to dryness under reduced pressure (2 kPa) at a temperature in the region of 40° C. The evaporation residue was purified by chromatography under an argon pressure of 50 kPa, on a column of silica gel (particle size 40–60 μm; diameter 3 cm), eluting with a successive mixture of cyclohexane-ethyl acetate (60/40 by volume) and then dichloromethane-methanol (90/10 by volume) and collecting 10-cm³ fractions. Fractions 1 to 21 were combined and then concentrated to dryness according to the conditions described above. 0.813 g of methyl (3RS,4RS)-4-[3-hydroxyimino-3-(3-fluoro-6-methoxyquinolin-4-yl)propyl]-1-[2-(2,5-difluorophenylthio)ethyl]piperidine-3-acetate were obtained in the form of a whitish viscous oil.

Infrared spectrum: (CCl₄)

3585; 3174; 2930; 1738; 1621; 1506; 1484; 1229; 1189; 1167; 1029; 909 and 833 cm⁻¹ d) Methyl (3RS,4RS)-4-[3-oxo-3-(3fluoro-6-methoxyquinolin-4-yl)propyl]-1-[2-(2,5-difluorophenylthio)ethyl]piperidine-3-acetate 1.88-cm³ of dimethyl sulfoxide in 6-cm³ of dichloromethane were poured, over 10 minutes, into a solution of 1.32-cm³ of oxalyl dichloride in 30-cm³ of dichloromethane cooled to −70° C., with stirring and under an inert atmosphere. After 10 minutes, a solution of 1.7 g of methyl (3RS,4RS)-4-[3-(R,S)-hydroxy-3-(3-fluoro-6-methoxyquinolin-4-yl)propyl]-1-[2-(2,5-difluorophenylthio)ethyl]piperidine-3-acetate in 15-cm³ of dichloromethane was poured in over 10 minutes. After 15 minutes, 8.4-cm³ of triethylamine in 10-cm³ of dichloromethane were added dropwise over 15 minutes and the reaction mixture was stirred for 45 minutes in the region of −70° C. and then for 20 hours in the region of 20° C. 50-cm³ of distilled water were poured over the reaction mixture, the organic phase was separated after settling out, washed with 50-cm³ of a saturated aqueous sodium hydrogen carbonate solution, twice with 30-cm³ of distilled water and 30-cm³ of a saturated aqueous sodium chloride solution. The organic extract was dried over magnesium sulfate, filtered and concentrated to dryness under reduced pressure (2 kPa) at a temperature in the region of 40° C. The residue obtained was purified by chromatography under an argon pressure of 50 kPa, on a column of silica gel (particle size 40–60 μm; diameter 3-cm), eluting with a cyclohexane-ethyl acetate (60/40 by volume) mixture and collecting 10-cm³ fractions. The fractions containing the expected product were combined and then concentrated to dryness according to the conditions described above. 1.37 g of methyl (3RS,4RS)-4-[3-oxo-3-(3-fluoro-6-methoxyquinolin-4-yl)propyl]-1-[2-(2,5-difluorophenylthio)ethyl]piperidine-3-acetate were obtained.

Infrared spectrum: (CCl₄) 2930; 1737; 1701; 1621; 1506; 1484; 1468; 1232; 1189; 1166; 1028; 905 and 834 cm⁻¹

EXAMPLE 7 a) (3RS,4RS)-4-[3-(R,S)-hydroxy-3-(3-fluoro-6-methoxyquinolin-4-yl)propyl]-1-(2,5-cyclopentanethio)ethylpiperidine-3-acetic Acid Hydrochloride A mixture of 0.12 g of methyl (3RS,4RS)-4-[3-(R,S)-hydroxy-3-(3-fluoro-6-methoxyquinolin-4-yl)propyl]-1-(2,5-cyclopentanethio)-ethyl-piperidine-3-acetate in 2-cm³ of dioxane and 0.6-cm³ of a 1 N aqueous sodium hydroxide solution was heated at a temperature in the region of 55° C., with stirring, for 18 hours. After cooling in the vicinity of 20° C., the reaction mixture was concentrated to dryness under reduced pressure (2 kPa) at a temperature in the region of 50° C. The evaporation residue was taken up in 5-cm³ of distilled water, acidified with a sufficient volume of a 1 N aqueous hydrochloric acid solution in order to obtain a pH in the region of 6. The mixture was extracted with 8-cm³ of dichloromethane and the organic phase was dried over magnesium sulfate, filtered and concentrated to dryness according to the same conditions described above. The residue was taken up in 5-cm³ of acetone and 1-cm³ of a 4 N hydrochloric acid solution in dioxane and then concentrated to dryness under reduced pressure (1 kPa) at a temperature in the region of 50° C. The residue was again taken up in 5-cm³ of acetone and concentrated to dryness according to the conditions described above. 0.078 g of (3RS,4RS)-4-[3-(R,S)-hydroxy-3-(3-fluoro-6-methoxyquinolin-4-yl)propyl]-1-(2,5-cyclopehtanethio)ethyl]piperidine-3-acetic acid hydrochloride were obtained in the form of an orange-colored pourer powder melting in the vinicinity of 125° C.

NMR spectrum ¹H NMR spectrum (400 MHz, (CD₃)₂SO d6 with addition of a few drops of CD₃COOD d4, at a temperature of 383K, δ in ppm): from 1.20 to 2.55 (mt: 18H); 2.89 (mt: 2H); from 3.00 to 3.35 (mt: 7H); 3.94 (s: 3H); 5.39 (mt: 1H); 7.39 (dd, J=9 and 2 Hz: 1H); 7.97 (d, J=9 Hz: 1H); 7.99 (mt: 1H); 8.63 (broad s: 1H).

b) Methyl (3RS,4RS)-4-[3-(R,S)-hydroxy-3-(3-fluoro-6-methoxyquinolin-4-yl)propyl]-1-(2,5-cyclopentanethio)ethylpiperidine-3-acetate A mixture of 1 g of methyl (3RS,4RS)-4-[3-(R,S)-hydroxy-3-(3-fluoro-6-methoxyquinolin-4-yl)propyl]piperidine-3-acetate hydrochloride, 0.424 g of (2-chloroethylthio)cyclopentane, 0.388 g of potassium iodide, 0.97 g of potassium carbonate and 0.656-cm³ of trietylamine in 30-cm³ of acetonitrile was heated, with stirring, for 18 hours at a temperature in the region of 65° C. After cooling to a temperature in the region of 20° C., the reaction mixture was filtered and the insoluble matter was washed twice with 20-cm³ of acetonitrile. The filtrate was concentrated to dryness under reduced temperature (1 kPa) at a temperature in the region of 50° C. The evaporation residue was taken up in 20-cm³ of distilled water and 30-cm³ of ethyl acetate. The organic phase was washed twice with 20-cm³ of distilled water and twice with 20-cm³ of a saturated aqueous sodium chloride solution, dried over magnesium sulfate, filtered and concentrated to dryness according to the conditions described above. The oil obtained was purified by chromatography under an argon pressure of 50 kPa, on a column of silica gel (particle size 40–60 μm, diameter 3 cm), eluting with a successive mixture of cyclohexane-ethyl acetate (60/40 by volume) and then dichloromethane-methanol (90/10 by volume) and collected 6-cm³ fractions. Fractions 6 to 25 were combined and then concentrated to dryness under reduced pressure (2 kPa) at a temperature in the region of 40° C. 0.42 g of methyl (3RS,4RS)-4-[3-(R,S)-hydroxy-3-(3-fluoro-6-methoxyquinolin-4-yl)propyl]-1-[2-(cyclopentanethio)ethyl]piperidine-3-acetate were obtained in the form of a yellow oil.

Infrared spectrum: (CCl₄)

3616; 2928; 2853; 1737; 1623; 1508; 1231; 1165; 1032; 907 and 834 cm⁻¹

The preparation of methyl (3RS,4RS)-4-[3-(R,S)-hydroxy-3-(3-fluoro-6-methoxyquinolin-4-yl)]propylpiperidine-3-acetate hydrochloride was described above.

EXAMPLE 8 a) Synthesis of Stereoisomers of 4-[3-hydroxy-3-(3-fluoro-6-methoxyquinolin-4-yl)propyl]-1-[2-(2-thienylthio)ethyl]piperidine-3-acetic Acid The absolute stereochemistry of each stereoisomer called hereinafter I, II, III, IV, V, VI, VII is not known.

Stereoisomer I

A solution of 0.625 g of methyl 4-[3-hydroxy-3-(3-fluoro-6-methoxyquinolin-4-yl)propyl]-1-[2-(2-(thienylthio)

ethyl)]piperidine-3-acetate (stereoisomer I) in 10-cm³ of dioxane and 3-cm³ of a 1 N aqueous sodium hydroxide solution was heated, with stirring, at a temperature in the region of 60° C. for 1 hour. After concentrating the reaction mixture under reduced pressure (5 kPa) at a temperature in the region of 40° C., the residue obtained was taken up in 10-cm³ of water, acidified with a 1 N aqueous hydrochloric acid solution. The precipitate formed was filtered, dried in an oven under a reduced pressure (10 Pa) at a temperature in the region of 20° C. for 18 hours. The product obtained was then stirred in 30-cm³ of acetone; a 4 N hydrochloric acid solution in dioxane was then poured in. The reaction mixture was concentrated under reduced pressure (5 kPa) at a temperature in the region of 40° C. and then the product was taken up with acetone 3 times by evaporating according to the conditions described above, at each stage. 0.42 g of 4-[3-hydroxy-3-(3-fluoro-6-methoxyquinolin-4-yl)propyl]-1-[2-(2-thienylthio)ethyl]piperidine-3-acetic acid dihydrochloride (stereoisomer I) were obtained in the form of a white solid. ($\alpha_D^{20}$=+56.9°+/−1.0 in methanol at 0.5%).

¹H NMR spectrum (400 MHz, $(CD_3)_2SO$ d6 with addition of a few drops of $CD_3COOD$ d4, at a temperature of 373K, δ in ppm): from 1.25 to 2.65 (mt: 9H); 2.33 (dd, J=15 and 5 Hz: 1H); from 3.05 to 3.40 (mt: 8H); 3.94 (s: 3H); 5.40 (broad t, J=7 Hz: 1H); 7.09 (mt: 1H); 7.28 (broad d, J=3 Hz: 1H); 7.37 (very broad d, J=9 Hz: 1H); 7.62 (broad d, J=5 Hz: 1H); from 7.90 to 8.00 (mt: 2H); 8.61 (broad s: 1H).

Stereoisomer II

A solution of 0.545 g methyl 4-[3-hydroxy-3-(3-fluoro-6-methoxyquinolin-4-yl)propyl]-1-[2-(2-(thienylthio)ethyl)]piperidine-3-acetate (stereoisomer II) in 10-cm³ of dioxane and 2.6-cm³ of a 1 N, aqueous sodium hydroxide solution was heated, with stirring, at a temperature in the region of 60° C., for 1 hour. After concentrating the reaction mixture under reduced pressure (5 kPa) at a temperature in the region of 40° C., the residue obtained was taken up, in 10-cm³ of water, acidified with a 1 N aqueous hydrochloric acid solution in order to obtain a pH equal to 6. The suspension was taken up in 20-cm³ of dichloromethane and then the organic phase was separated after settling out, dried over magnesium sulfate, filtered, and concentrated under reduced pressure (5 kPa) at a temperature in the region of 40° C. The product obtained was then stirred in 20-cm³ of acetone and a 4 N hydrochloric acid solution was poured into dioxane. The precipitate formed was filtered, dried in an oven under reduced pressure (10 Pa) at a temperature in the region of 20° C. for 18 hours. The residue obtained was then taken up in acetone several times while evaporating according to the conditions described above, at each stage. 0.43 g of 4-[3-hydroxy-3-(3-fluoro-6-methoxyquinolin-4-yl)propyl]-1-[2-(2-thienylthio)ethyl]piperidine-3-acetic acid dihydrochloride (stereoisomer II) were obtained in the form of a white solid. ($\alpha_D^{20}$=+55.9°+/−0.9 in methanol at 0.5%).

¹H NMR spectrum (400 MHz, $(CD_3)_2SO$ d6 with addition of a few drops of $CD_3COOD$ d4, at a temperature of 373K, δ in ppm): from 1.25 to 2.60 (mt: 10H); from 3.00 to 3.40 (mt: 8H); 3.94 (s: 3H); 5.39 (dd, J=7 and 5 Hz: 1H); 7.09 (dd, J=5 and 3 Hz: 1H); 7.28 (broad d, J=3 Hz: 1H); 7.38 (dd, J=9 and 2.5 Hz: 1H); 7.63 (broad d, J=5 Hz: 1H); from 7.90 to 8.05 (mt: 2H); 8.63 (broad s: 1H).

Stereoisomer III

A solution of 0.458 g of methyl 4-[3-hydroxy-3-(3-fluoro-6-methoxyquinolin-4-yl)propyl]-1-[2-(2-(thienylthio)ethyl)]piperidine-3-acetate (stereoisomer III) in 10-cm³ of dioxane and 2.2-cm³ of a 1 N aqueous sodium hydroxide solution was heated, with stirring at a temperature in the region of 60° C., for 1 hour. After concentrating the reaction mixture under reduced pressure (5 kPa) at a temperature in the region of 40° C., the residue obtained was taken up in 10-cm³ of water, acidified with an aqueous acetic acid solution in order to obtain a pH equal to 6. The suspension was taken up in 20-cm³ of dichloromethane and then the organic phase was separated after settling out, dried over magnesium sulfate, filtered, and concentrated under reduced pressure (5 kPa) at a temperature in the region of 40° C. The product obtained was then stirred in 20-cm³ of acetone; a 4 N hydrochloric acid solution in dioxane was then poured in. The precipitate formed was filtered, dried in an oven under reduced pressure (10 Pa) at a temperature in the region of 20° C. for 18 hours. The residue obtained was then taken up in acetone several times while evaporating according to the conditions described above at each stage. 0.42 g of 4-[3-hydroxy-3-(3-fluoro-6-methoxyquinolin-4-yl)propyl]-1-[2-(2-thienylthio)ethyl]piperidine-3-acetic acid (stereoisomer III) in the form of a white solid were obtained. $\alpha_D^{20}$=−46.9°+/−0.9 in methanol at 0.5%).

¹H NMR spectrum (400 MHz, $(CD_3)_2SO$ d6 with addition of a few drops of $CD_3COOD$ d4, at a temperature of 373K, δ in ppm): from 1.25 to 2.60 (mt: 10H); from 3.00 to 3.40 (mt: 8H); 3.94 (s: 3H); 5.39 (broad t, J=7 Hz: 1H); 7.09 (mt: 1H); 7.28 (broad d, J=3 Hz: 1H); 0.7.38 (very broad d, J=9 Hz: 1H); 7.63 (broad d, J=5 Hz: 1H); from 7.90 to 8.05 (mt: 2H); 8.62 (broad s: 1H).

Stereoisomer IV

A solution of 0.454 g of methyl 4-[3-hydroxy-3-(3-fluoro-6-methoxyquinolin-4yl)propyl]-1-[2-(2-(thienylthio)ethyl)]piperidine-3-acetate (stereoisomer IV) in 10-cm³ of dioxane and 2.2-cm³ of a 1 N aqueous sodium hydroxide solution was heated with stirring at a temperature in the region of 60° C., for 1 hour. After concentrating the reaction mixture under reduced pressure (5 kPa) at a temperature in the region of 40° C., the residue obtained was taken up in 10-cm³ of water, acidified with an aqueous acetic acid solution in order to obtain a pH equal to 6. The suspension was taken up in 20-cm³ of dichloromethane and then the organic phase was separated after settling out, dried over magnesium sulfate, filtered, concentrated under reduced pressure (5 kPa) at a temperature in the region of 40° C. The product obtained was then stirred in 20-cm³ of acetone and a 4 N hydrochloric acid solution in dioxane was poured in. The precipitate formed was filtered, and dried in an oven under a reduced pressure (10 Pa) at a temperature in the region of 20° C. for 18 hours. The residue obtained was then taken up in acetone several times while evaporating according to the conditions described above, at each stage. 0.35 g of 4-[3-hydroxy-3-(3-fluoro-6-methoxyquinolin-4-yl)propyl]-1-[2-2-thienylthio)ethyl]piperidine-3-acetic acid dihydrochloride (stereoisomer IV) were obtained in the form of a white solid. ($\alpha_D^{20}$=−54.8°+/−1.1 in methanol at 0.5%).

¹H NMR spectrum (400 MHz, $(CD_3)_2SO$ d6 with addition of a few drops of $CD_3COOD$ d4, at a temperature of 373K, δ in ppm): from 1.25 to 2.60 (mt: 9H); 2.22 (broad dd, J=15 and 5 Hz: 1H) from 3.00 to 3.40 (mt: 8H); 3.94 (s: 3H); 5.40 (mt: 1H); 7.10 (mt: 1H); 7.29 (broad d, J=3 Hz: 1H); 7.38 (very broad d, J=9 Hz: 1H); 7.64 (broad d, J=5 Hz,: 1H); from 7.90 to 8.05 (mt: 2H); 8.62 (broad s: 1H).

Stereoisomer V

A solution of 0.560 g of methyl 4-[3-hydroxy-3-(3-fluoro-6-methoxyquinolin-4yl)propyl]-1-[2-(2-(thienylthio)ethyl)]piperidine-3-acetate (stereoisomer V) in 10-cm³ of dioxane and 2.2-cm³ of a 1 N aqueous sodium hydroxide solution was heated with stirring at a temperature in the region of 60° C., for 2 hours. After concentrating the reaction mixture under reduced pressure (5 kPa) at a temperature in the region of 40° C., the residue obtained was taken up in 10-cm³ of water, acidified with an aqueous acetic acid solution in order to obtain a pH equal to 6. The suspension was taken up in 20-cm³ of dichloromethane and then the organic phase was separated after settling out, dried over magnesium sulfate, filtered, and concentrated under reduced pressure (5 kPa) at a temperature in the region of 40° C. The product obtained was then stirred in 20-cm³ of acetone; a 4 N hydrochloric acid solution in dioxane was then poured in. The precipitate formed was concentrated under reduced pressure (5 kPa) at a temperature in the region of 40° C. The residue obtained was then taken up in acetone several times while evaporating according to the conditions described above at each stage, and then dried in an oven under a reduced pressure (10 Pa) at a temperature in the region of 20° C. for 120 hours. 0.4 g of 4-[3-hydroxy-3-(3-fluoro-6-methoxyquinolin-4-yl) propyl]-1-[2-2-thienylthio)ethyl]piperidine-3-acetic acid were obtained (stereoisomer V) in the form of a white solid. $\alpha_D^{20}$=+83.4°+/−1.3 in methanol at 0.5%).

$^1$H NMR spectrum (400 MHz, (CD$_3$)$_2$SO d6, δ in ppm): 0.95 (mt: 1H); 1.41 (mt: 2H); from 1.65 to 2.15 (mt: 6H); 2.36 (dd, J=16.5 and 3.5 Hz: 1H); from 2.70 to 2.90 (mt: 2H); 3.13 (mt: 2H); 3.20 (mt: 2H); from 3.35 to 3.55 (mt: 2H); 3.91 (s: 3H); 5.32 (broad t, J=7.5 Hz: 1H); 7.10 (dd, J=5.5 and 3.5 Hz: 1H); 7.28 (dd, J=3.5 and 1 Hz: 1H); 7.38 (dd, J=9 and 3 Hz: 1H); 7.68 (dd, J=5.5 and 1 Hz: 1H); 7.94 (mt: 1H); 7.96 (d, J=9 Hz: 1H); 8.70 (d, J=1.5 Hz: 1H); 10.15 (unresolved complex: 1H).

Stereoisomer VI

A solution of 0.36 g of methyl 4-[3-hydroxy-3-(3-fluoro-6-methoxyquinolin-4-yl)propyl]-1-[2-(2-(thienylthio) ethyl)]piperidine-3-acetate stereoisomer VI) in 10-cm³ of dioxane and 1.7-cm³ of a 1 N aqueous sodium hydroxide solution was heated with stirring at a temperature in the region of 60° C., for 2 hours. After concentrating the reaction mixture under reduced pressure (5 kPa) at a temperature in the region of 40° C., the residue obtained was taken up in 10-cm³ of water, acidified with an aqueous acetic acid solution in order to obtain a pH equal to 6. The suspension was taken up in twice 10-cm³ of dichloromethane and then the organic phase was separated after settling out, dried over magnesium sulfate, filtered, concentrated under reduced pressure (5 kPa) at a temperature in the region of 40° C. The product obtained was then stirred in 20-cm³ of acetone; a 4 N hydrochloric acid solution in dioxane was poured in. The precipitate formed was concentrated under reduced pressure (5 kPa) at a temperature in the region of 40° C. The residue obtained was then taken up in acetone several times while evaporating according to the conditions described above at each stage, and then dried in an oven under a reduced pressure (10 Pa) at a temperature in the region of 20° C. for 48 hours. 0.325 g of 4-[3hydroxy-3-(3-fluoro-6-methoxyquinolin-4-yl)propyl]-1-[2-2-thienylthio)ethyl]piperidine-3-acetic acid dihydrochloride (stereoisomer VI) were obtained in the form of a white solid. $\alpha_D^{20}$=+29.8°+/−0.8 in methanol at 0.5%).

$^1$H NMR spectrum (300 MHz, (CD$_3$)$_2$SO d6, δ in ppm),: from 1.30 to 2.20 (mt: 9H); 2.46 (mt: 1H); from 2.70 to 2.95 (mt: 2H); from 3.10 to 3.30 (mt: 4H); from 3.35 to 3.65 (mt: 2H); 3.91 (s: 3H); 5.32 (dd, J=8 and 6 Hz: 1H); 7.12 (dd, J=5.5 and 3.5 Hz: 1H); 7.31 (dd, J=3.5 and 1 Hz: 1H); 7.40 (dd, J=9 and 3 Hz: 1H); 7.72 (dd, J=5.5 and 1 Hz: 1H); 7.96 (d, J=9 Hz: 1H); 7.98 (mt: 1H); 8.70 (d, J=1.5 Hz: 1H); 9.93 (unresolved complex: 1H).

Stereoisomer VII

A solution of 0.39 g of methyl 4-[3-hydroxy-3-(3-fluoro-6-methoxyquinolin-4-yl)propyl]-1-[2-(2-(thienylthio) ethyl)]piperidine-3-acetate (stereoisomer VII) in 10-cm³ of dioxane and 1.8-cm³ of a 1 N aqueous sodium hydroxide solution was heated, with stirring at a temperature in the region of 60° C., for 2 hours. After concentrating the reaction mixture under reduced pressure (5 kPa) at a temperature in the region of 40° C., the residue obtained was taken up in 10-cm³ of water and acidified with an aqueous acetic acid solution in order to obtain a pH equal to 6. The suspension was taken up in 20-cm³ of dichloromethane and then the organic phase was separated after settling out, dried over magnesium sulfate, filtered, and concentrated under reduced pressure (5 kPa) at a temperature in the region of 40° C. The product obtained was then stirred in 20-cm³ of acetone; a 4 N hydrochloric acid solution in dioxane was then poured in. The precipitate formed was concentrated under reduced pressure (5 kPa) at a temperature in the region of 40° C. The residue obtained was then taken up in acetone several times while evaporating according to the conditions described above at each stage, and then dried in an oven under a reduced pressure (10 Pa) at a temperature in the region of 20° C. for 48 hours. 0.4 g of 4-[3-hydroxy-3-(3-fluoro-6-methoxyquinolin-4-yl)propyl]1-[2-(2-thienylthio) ethyl]piperidine-3-acetic acid dihydrochloride (stereoisomer VII) were obtained in the form of a white solid ($\alpha_D^{20}$=−27.1°+/−0.7 in methanol at 0.5%).

$^1$H NMR spectrum (300 MHz, (CD$_3$)$_2$SO d6, δ in ppm): from 1.30 to 2.20 (mt: 9H); 2.45 (mt: 1H); from 2.70 to 2.95 (mt: 2H); from 3.10 to 3.30 (mt: 4H); from 3.35 to 3.70 (mt: 2H); 3.91 (s: 3H); 5.32 (dd, J=8 and 6 Hz: 1H); 7.10 (dd, J=5.5 and 3.5 Hz: 1H); 7.30 (dd, J=3.5 and 1 Hz: 1H); 7.39 (dd, J=9 and 3 Hz: 1H); 7.71 (dd, J=5.5 and 1 Hz: 1H); 7.95 (d, J=9 Hz: 1H); 7.97 (mt: 1H); 8.68 (d, J=1.5 Hz: 1H); 9.96 (unresolved complex: 1H).

b) Synthesis of Stereoisomers of Methyl 4-[3-hydroxy-3-(3-fluoro-6-methoxyquinolin-4-yl)propyl]-1-[2-(2-(thienylthio)ethyl)]piperidine-3-acetate A mixture of 11.9 g of methyl 4-[3-hydroxy-3-(3-fluoro-6-methoxyquinolin-4-yl)propyl]piperidine-3-acetate hydrochloride, 4.5 g of 2-(2-bromoethylthio)thiophene, 3 g of potassium iodide, 7.5 g of potassium carbonate and 5-cm³ of triethylamine in 200-cm³ of acetonitrile and 100-cm³ of dimethylformamide was heated, with stirring, for 16 hours at a temperature in the region of 65° C. The reaction mixture was filtered and the filtrate was concentrated to dryness under reduced pressure (1 kPa) at a temperature in the region of 50° C. The evaporation residue was purified by chromatography under an argon pressure of 40 kPa, on a column of silica gel (particle size 40–60 μm; diameter 8 cm, height 40 cm), eluting with a cyclohexane-ethyl acetate (50/50by volume) mixture, collecting 200-cm³ fractions after the passage of 3 dm³ of a cyclohexane-ethyl acetate (50/50 by volume) mixture. Fractions 20 to 40 were combined and then concentrated to dryness under reduced pressure (2 kPa) at a temperature in the region of 40° C. in order to obtain 3.1 g of a mixture of stereoisomers I, II, III, IV, in the form of a yellow oil. Fractions 48 to 90 were combined and then concentrated to dryness under reduced pressure (2 kPa) at a temperature in the region of 40° C. in order to obtain 3.8 g of a mixture of stereoisomers V, VI, VII, VIII, in the form of a yellow oil.

The absolute stereochemistry of each stereoisomer (esters) called hereinafter I, II, III, IV V, VI, VII, VIII is not known.

Starting with the Mixture of Stereoisomers I, II, III, IV Obtained above, the Separation of each Stereoisomer was Carried Out by HPLC The separation of 2 pairs of stereoisomers (I+II) and (III+IV) was carried out on a stationary chiral phase starting with 22.7 g of the I, II, III, IV mixture described above in Example 8b, (type of phase: chiracel OD; particle size 20 μmm; diameter 80 mm; mixture of the stationary phase 1.2 kg), under a pressure of 600 kPa, the mobile phase was composed of a mixture of heptane-2-propanol (90/10 by volume) having a flow rate of 160-cm$^3$ per minute and the UV detector wavelength was set at 265 nm. The fractions containing a first pair of diastereoismers noted (I+II) were combined and concentrated to dryness under reduced pressure (2 kPa) at a temperature in the region of 40° C. and 1.3 g were obtained in the form of an oil with a recovery rate equal to 96%. The fractions containing the second pair of diastereoismers noted (III+IV) were combined and concentrated to dryness under reduced pressure (2 kPa) at a temperature in the region of 40° C. and 1.03 g thereof were obtained in the form of an oil with a recovery rate equal to 76%. Next, the products of each pair of stereoisomers (I–II and III–IV respectively) were separated on a chiralpak AD column (particle size 20 μmm; diameter 80 mm; mass of the stationary phase 1.2 kg) under a pressure of 800 kPa, the mobile phase was composed of a mixture of heptane-ethanol (90/10 by volume) having a flow rate of 200-cm$^3$ per minute and the UV detector wavelength was set at 280 nm. The fractions containing each product were isolated and then concentrated under reduced pressure (2 kPa) at a temperature in the region of 40° C.; 0.632 g of the stereoisomer I, 0.553 g of the stereoisomer II, 0.463 g of the stereoisomer III, 0.46 g of the stereoisomer IV were thus obtained.

NMR spectrum of stereoisomer I: $^1$H (300 MHz, (CD$_3$)$_2$SO d6, δ in ppm): from 0.85 to 1.55 (mt: 6H); from 1.75 to 2.10 (mt: 6H); from 2.35 to 2.55 (mt: 2H); from 2.55 to 2.80 (mt: 2H); 2.87 (t, J=7 Hz: 2H); 3.50 (s: 3H); 3.89 (s: 3H); 5.33 (broad t, J=7 Hz: 1H); 5.82 (broad s: 1H); 7.04 (dd, J=5.5 and 3.5 Hz: 1H); 7.15 (dd, J=3.5 and 1.5, Hz: 1H); 7.38 (dd, J=9 and 3 Hz: 1H); 7.60 (dd, J=5.5 and 1.5 Hz 1H); from 7.90 to 8.00 (mt: 2H); 8.68 (d, J=2 Hz: 1H).

HPLC condition: Chiralpack® column, flow rate 1-cm$^3$/min, elution condition
from 0 to 13 min: ethanol-heptane (7/93 by volume)
from 13 to 28 min (in a gradient) ethanol-heptane (15/93 by volume)
from 28 to 35 min (in a gradient) ethanol-heptane (7/93 by volume)
Retention time: 24.13 min NMR spectrum of stereoisomer II: $^1$H (300 MHz, (CD$_3$)$_2$SO d6, δ in ppm): from 1.00 to 1.55 (mt: 6H); from 1.70 to 2.15 (mt: 5H); 2.21 (dd, J=16 and 3 Hz: 1H); from 2.30 to 2.60 (mt: 2H); 2.67 (mt: 2H); 2.89 (t, J=7 Hz: 2H); 3.59 (s: 3H); 3.90 (s: 3H); 5.34 (mt: 1H); 5.83 (very broad d, J=3 Hz: 1H); 7.05 (dd, J=5.5 and 3.5 Hz: 1H); 7.17 (broad dd, J=3.5 and 1.5 Hz: 1H); 7.39 (dd, J=9 and 3 Hz: 1H); 7.61 (dd, J=5.5 to 1.5 Hz: 1H); 7.96 (d, J=9 Hz: 1H); 7.99 (mt: 1H); 8.69 (broad s: 1H).

HPLC condition: Chiralpack® column, low rate 1-cm$^3$/min, elution condition
from 0 to 13 min: ethanol-heptane (7/93 by volume)
from 13 to 28 min (in a gradient) ethanol-heptane (15/93 by volume)
from 28 to 35 min (in a gradient) ethanol-heptane (7/93 by volume)
Retention time: 29.04 min NMR spectrum of stereoisomer III: $^1$H (300 MHz, (CD$_3$)$_2$SO d6, δ in ppm): from 1.00 to 1.55 (mt: 6H); from 1.70 to 2.15 (mt: 5H); 2.21 (dd, J=16 and 3.5 Hz: 1H); from 2.30 to 2.60 (mt: 2H); 2.67 (mt: 2H); 2.88 (t, J=7 Hz: 2H); 3.58 (s: 3H); 3.90 (s: 3H); 5.33 (mt: 1H); 5.82 (broad s: 1H); 7.04 (dd, J=5.5 and 3.5 Hz: 1H); 7.16 (dd, J=3.5 and 1.5 Hz: 1H); 7.38 (dd, J=9 and 3 Hz: 1H); 7.59 (dd, J=5.5 and 1.5 Hz: 1H); 7.96 (d, J=9 Hz: 1H); 7.97 (mt: 1H); 8.68 (broad d, J=1.5 Hz: 1H).

HPLC condition: Chiralpack® column, flow rate 1-cm$^3$/min, elution condition
from 0 to 13 min: ethanol-heptane (7/93 by volume)
from 13 to 28 min (in a gradient) ethanol-heptane (15/93 by volume)
from 28 to 35 min (in a gradient) ethanol-heptane (7/93 by volume)
Retention time: 23 min NMR spectrum of stereoisomer IV: $^1$H (300 MHz, (CD$_3$)$_2$SO d6, δ in ppm): from 0.90 to 1.55 (mt: 6H); from 1.75 to 2.10 (mt: 6H); from 2.35 to 2.55 (mt: 2H); from 2.55 to 2.80 (mt: 2H); 2.87 (t, J=7 Hz: 2H); 3.50 (s: 3H); 3.90 (s: 3H); 5.35 (mt: 1H); 5.83 (d, J=3 Hz: 1H); 7.04 (dd, J=5.5 and 3.5 Hz: 1H); 7.15 (broad dd, J=3.5 and 1.5 Hz: 1H); 7.38 (dd, J=9 and 3 Hz: 1H); 7.60 (broad dd, J=5.5 and 1.5 Hz: 1H); from 7.90 to 8.00 (mt: 2H); 8.69 (broad s: 1H).

HPLC condition: Chiralpack® column, flow rate 1-cm$^3$/min, elution condition
from 0 to 13 min: ethanol-heptane (7/93 by volume).
from 13 to 28 min (in a gradient) ethanol-heptane (15/93 by volume)
from 28 to 35 min (in a gradient) ethanol-heptane (7/93 by volume)
Retention time: 25.38 min Starting with the Mixture of Stereoisomers V, VI, VII, VIII Obtained above, the Separation of each Stereoisomer was Carried Out by HPLC The separation of the 2 pairs of stereoisomers was carried out on a C18 stationary phase starting with 3.5 g of the V, VI, VII, VIII mixture described above (type of phase: KROMACIL® C18; particle size 7 μm; diameter 4.6 mm; mass of the stationary phase 1 kg), under a pressure of 5000 kPa, the mobile phase was composed of a mixture of water-acetonitrile-methanol-trifluoroacetic acid (60/15/25/0.05 by volume) having a flow rate of 140-cm$^3$ per minute and the UV detector wavelength was set at 254 nm. The fractions containing the first pair of stereoisomers noted (V+VIII) were combined and concentrated to dryness under reduced pressure (2 kPa) at a temperature in the region of 40° C. and 1.84 g thereof were obtained in the form of an oil. The fractions containing the second pair of stereoisomers noted (VI+VII) were combined and concentrated to dryness under reduced pressure (2 kPa) at a temperature in the region of 40° C. and 1.42 g thereof were obtained in the form of an oil. Next, the enantiomers of the pair of stereoisomers (V+VIII) were separated on a CHIRALPAK® AS column (particle size 20 μm; diameter 80 mm; mass of the stationary phase 1.2 kg) under a pressure of 290 kPa, the mobile phase was composed of a mixture of isopropanol-heptane-triethylamine (10/90/0.1 by volume) having a flow rate of 110-cm$^3$ per minute and the UV detector wavelength was set at 265 nm. The fractions containing each enantiomer were isolated and then concentrated under a reduced pressure (2 kPa) at a temperature in the region of 40° C.; 0.5 g of stereoisomer V were thus obtained, the enantiomers of the pair of stereoisomers VI+VII were separated on an OC type CHIRALCEL® column (particle size 10 μm; diameter 60 mm; mass of the stationary phase 600 g) under a pressure of 230 kPa, the mobile phase was composed of an ethanol-heptane-triethylamine (10/90/0.1 by volume) mixture having a flow rate of 90-cm$^3$ per minute and the UV detector wavelength was set at 265 nm. The fractions containing each enantiomer were isolated and then concentrated under reduced pressure (2 kPa) at a temperature in the region of 40° C.; 0.36 g of stereoisomer VI and 0.68 g of stereoisomer VII were thus obtained.

$^1$H NMR spectrum stereoisomer V: (300 MHz, (CD$_3$)$_2$SO d6, δ in ppm): from 0.80 to 2.00 (mt: 8H); 2.08 (broad dd, J=16.5 and 8 Hz: 1H); 2.35 (dd, J=16.5 and 4 Hz: 1H); from 2.20 to 3.30 (mt: 8H); 3.55 (s: 3H); 3.92 (s: 3H); 5.33 (mt: 1H); 5.88 (d, J=4 Hz: 1H); 7.08 (dd, J=5.5 and 3.5 Hz: 1H); 7.25 (broad d, J=3.5 Hz: 1H); 7.42 (dd, J=9 and 3 Hz: 1H); 7.68 (dd, J=5.5 and 1 Hz: 1H); 7.95 (mt: 1H); 7.97 (d, J=9 Hz: 1H); 8.69 (broad d, J=1.5 Hz: 1H); from 8.90 to 10.00 (unresolved complex: 1H).

HPLC condition: separation on Chiralpak AS 20 μm phase.

Elution condition: heptane, ethanol, trethylamine (85/15/0.1% volume); 1 ml/min

UV 254 nm

Retention time: 9.37 min $^1$H NMR spectrum stereoisomer VI: (300 MHz, (CD$_3$)$_2$SO d6, δ in ppm): from 1.00 to 2.65 (mt: 12H); 2.06 (dd, J=15.5 and 7.5 Hz: 1H); 2.40 (dd, J=15.5 and 4 Hz: 1H); from 2.65 to 2.90 (mt: 2H); 2.91 (broad t, J=7 Hz: 2H); 3.54 (s: 3H); 3.90 (s: 3H); 5.32 (mt: 1H); 5.84 (d, J=4 Hz: 1H); 7.05 (dd, J=5.5 and 3.5 Hz: 1H); 7.16 (dd, J=3.5 and 1.5 Hz: 1H); 7.39 (dd, J=9 and 3 Hz: 1H); 7.61 (dd, J=5.5 and 1.5 Hz: 1H); 7.96 (d, J=9 Hz: 1H); 7.99 (mt: 1H); 8.68 (broad d, J=1.5 Hz: 1H).

HPLC conditions for the separation on a Chiracel OC 10 μm column

Elution condition: heptane, ethanol, triethylamine (90/10/0.1% by volume); 1 ml/min; UV 254 nm.

Retention time: 17.5 min $^1$H NMR spectrum stereoisomer VII: (300 MHz, (CD$_3$)$_2$SO d6, δ in ppm): from 1.00 to 2.65 (mt: 12H); 2.05 (dd, J=15 and 7.5 Hz: 1H); 2.40 (dd, J=15 and 4 Hz: 1H); 2.79 (mt: 2H); 2.93 (broad t, J=7 Hz: 2H); 3.56 (s: 3H); 3.90 (s: 3H); 5.31 (mt: 1H); 5.84 (d, J=4 Hz: 1H); 7.05 (dd, J=5.5 and 3.5 Hz: 1H); 7.19 (broad d, J=3.5 Hz: 1H); 7.40 (dd, J=9 and 3 Hz: 1H); 7.62 (dd, J=5.5 and 1 Hz: 1H); 7.96 (d, J=9 Hz: 1H); 7.99 (mt: 1H); 8.68 (broad d, J,=1.5 Hz: 1H).

HPLC Conditions for the Separation on a Chiracel OC 10 μm Column

Elution condition: heptane, ethanol, triethylamine (90/10/0.1% by volume); 1 ml/min;

UV 254 nm.

Retention time: 23.76 min

EXAMPLE 9 a) (3RS,4RS)-4-[3-(R,S)-hydroxy-3-(3-fluoro-6-methoxy-quinoline-4-yl)propyl]-1-[3-(2,3,5-Trifluorophenyl)prop-2-ynyl]piperidin-3-yl)acetic Acid Dihydrochloride A mixture of 0.97 g of methyl (3RS,4RS)-4-[3-(R,S)-hydroxy-3-(3-fluoro-6-methoxy-quinoline-4-yl)propyl]-1-[3-(2,3,5-trifluorophenyl)prop-2-ynyl]piperidin-3-yl-acetate in 30-cm$^3$ of dioxane and 4-cm$^3$ of a 1 N aqueous sodium hydroxide solution was heated at a temperature in the region of 50° C. with stirring for 18 hours. After cooling in the vicinity of 20° C., the reaction mixture was concentrated to dryness under reduced pressure (2 kPa) at a temperature in the region of 50° C. The evaporation residue was taken up in 10-cm$^3$ of distilled water, acidified with a sufficient volume of a 1 N aqueous hydrochloric acid solution in order to obtain a pH in the region of 4. The mixture was extracted twice with 15-cm$^3$ of dichloromethane and the organic phase was dried over magnesium sulfate, filtered and concentrated to dryness according to the same conditions described above. The residue was taken up in 5-cm$^3$ of acetone and 1-cm$^3$ of a hydrochloric acid solution in dioxane and then concentrated to dryness under reduced pressure (1 kPa) at a temperature in the region of 50° C. The residue was again taken up in 5-cm$^3$ of acetone and concentrated to dryness according to the same conditions described above. 0.69 g of (3RS,4RS)-4-[3-(R,S)-hydroxy-3-(3-fluoro-6-methoxyquinolin-4-yl)propyl]-1-[3-(2,3,5-trifluorophenyl)prop-2-ynyl]piperidin-3-yl-acetic acid dihydrochloride were obtained in the form of a solid melting in the vicinity of 135° C.

Infrared-spectrum: (KBr tablet): 3126; 2938; 2541; 2022; 1720; 1628; 1604; 1555; 1498; 1448; 1421; 1308; 1243; 1180; 1141; 1097; 1000; 870 and 780 cm-1 b) Methyl (3RS,14RS)-4-[3-(R,S)-hydroxy-3-(3-fluoro-6-methoxyquinolin-4-yl)propyl]-1-[3-(2,3,5-trifluorophenyl)prop-2-ynyl]piperidin-3-yl-acetate A mixture of 1.7 g of methyl (3RS,4RS)-4-[3-(R,S)-hydroxy-3-(3-fluoro-6-methoxyquinolin-4-yl)propyl]-1-(prop-2-ynyl)piperidine-3-carboxylate, 0.077 g of copper iodide, 1.2 g of 1-bromo-2,3,5-trifluorobenzene, 0.23 g of 2-tetrakis(triphenylphosphine)palladium(0) in 17-cm$^3$ of triethylamine was heated at a temperature in the region of 80° C. with stirring for 8 hours. After cooling in the region of 20° C., the reaction mixture was concentrated to dryness under reduced pressure (2 kPa) at a temperature in the region of 50° C. The evaporation residue was taken up in 20-cm$^3$ of ethyl acetate, washed 3 times with 15-cm$^3$ of distilled water, dried over magnesium sulfate, filtered and concentrated to dryness according to the same conditions described above. The residue was purified by chromatography under an argon pressure of 50 kPa, on a column of silica gel (particle size 40–60 μm; diameter 3 cm), eluting with a mixture of cyclohexane-ethyl acetate (80/20 by volume) and collecting 15-cm$^3$ fractions. Fractions 48 to 78 were combined and then concentrated to dryness according to the same conditions described above. 0.97 g of methyl (3RS,4RS)-4-[3-(R,S)-hydroxy-3-(3-fluoro-6-methoxyquinolin-4-yl)propyl]-1-[3-(2,3,5-trifluorophenyl)prop-2-ynyl]piperidin-3-yl}acetate were obtained in the form of an oil.

Infrared spectrum (CCl$_4$): 3618; 3089; 2935; 2804; 2766; 2223; 1737; 1623; 1508; 1496; 1232; 1166; 1132; 1075; 999, 861 and 834 cm-1

EXAMPLE 10 a) (3RS,4RS)-4-[3-(R,S)-hydroxy-3-(3-fluoro-6-methoxyquinolin-4-yl)propyl]-1-[2-(2-thienylthio)ethyl]piperidine-3-carboxylic Acid Dihydrochloride A solution of 630 mg of methyl (3RS,4RS)-4-[3-(R,S)-hydroxy-3-(3-fluoro-6-methoxyquinolin-4-yl)propyl]-1-[2-(2-thienylthio)ethyl]piperidine-3-carboxylate, 6-cm$^3$ of dioxane and 3-cm$^3$ of a 1 N aqueous sodium hydroxide solution was heated with stirring at a temperature in the region of 60° C. for 2 hours. 3-cm$^3$ of a 1 N aqueous sodium hydroxide solution were added and the solution was heated for 1 hour at 60° C. After concentrating the reaction mixture under reduced pressure (5 kPa) at a temperature in the region of 40° C., the residue obtained was taken up in 20-cm$^3$ of water and 20-cm$^3$ of diethyl ether. The aqueous phase was separated after settling out and was then acidified by pouring in 6-cm$^3$ of 1 N hydrochloric acid. The white precipitate formed was extracted with 150-cm$^3$ of ethyl acetate. The organic phase was washed twice with 10-cm$^3$ of a saturated aqueous sodium chloride solution and dried over magnesium sulfate, filtered, and then concentrated under reduced pressure (5 kPa) at a temperature in the region of 40° C. 499 mg of (3RS,4RS)-4-[3-(R,S)-hydroxy-3-(3-fluoro-6-methoxyquinolin-4-yl)propyl]-1-[2-(2-thienylthio)ethyl]piperidine-3-carboxylic acid were obtained in the form of a white solid.

¹H NMR spectrum (300 MHz, (CD₃)₂SO d6 with, δ in ppm). A mixture of stereoisomers in the proportions 50/50 was observed.

\* from 0.90 to 2.25 (mt: 10H); from 2.45 to 2.65 (mt: 2H); from 2.70 to 3.05 (mt: 4H); 3.92 (s: 3H); 5.31 (mt: 1H); from 5.50 to 6.20 (broad unresolved complex: 1H); 7.04 (mt: 1H); 7.18 (mt: 1H); 7.38 (mt: 1H); 7.59 (mt: 1H); from 7.90 to 8.05 (mt: 2H); 8.67 (mt: 1H); from 11.50 to 13.50 (very broad unresolved complex).

b) Methyl (3RS,4RS)-4-[3-(R,S)-hydroxy-3-(3-fluoro-6-methoxyquinolin-4-yl)propyl]-1-[2-(2-thienylthio)ethyl]piperidine-3-carboxylate 0.74-cm³ of triethylamine was added to a solution composed of 1.17 g of methyl (3RS, 4RS)-4-[3-(R,S)-hydroxy-3-(3-fluoro-6-methoxyquinolin-4-yl)propyl]piperidine-3-carboxylate dihydrochloride in 20-cm³ of acetonitrile and 10 cm³ of DMF, followed by 638 mg of 2-(2-bromoethylthio)thiophene in 10 cm³ of acetonitrile, 1 g of potassium carbonate and 431 mg of potassium iodide. The mixture was stirred for 15 hours at a temperature in the region of 65° C. under an inert atmosphere. After cooling to about 20° C., the reaction mixture was filtered on sintered glass. The filtrate was taken up in 100-cm³ of acetonitrile and concentrated under reduced pressure (5 kPa). The residue was taken up in 200-cm³ of ethyl acetate and 100-cm³ of water. The organic phase was separated after settling out, washed with twice 75-cm³ of a saturated aqueous sodium chloride solution, dried over magnesium sulfate, filtered, and concentrated under reduced pressure (5 kPa) at a temperature in the region of 40° C. The residue obtained was purified by chromatography, under a nitrogen pressure of 50 kPa, on a column of silica gel (particle size 20–45μ; diameter 2 cm; height 40 cm), eluting with a mixture of cyclohexane-ethyl acetate (25/75 by volume) and collecting 50-cm³ fractions. Fractions 6 to 8 were concentrated. 630 mg of methyl (3RS,4RS)-4-[3-(R,S)-hydroxy-3-(3-fluoro-6-methoxyquinolin-4-yl)propyl]-1-[2-(2-thienylthio)ethyl]piperidine-3-carboxylate were obtained in the form of a colorless oil.

Infrared spectrum (CCl₄): 3616; 2950; 2811; 2770; 1739; 1623; 1508; 1497; 1354; 1232; 1158; 1133; 1034; 907; 834 and 700 cm-1 c) Methyl (3RS,4RS)-4-[3-(R,S)-hydroxy-3-(3-fluoro-6-methoxyquinolin-4-yl)propyl]piperidine-3-carboxylate Dihydrochloride A solution of 1.26 g of (3RS,4RS)-4-[3-(R,S)-hydroxy-3-(3-fluoro-6-methoxyquinolin-4-yl)propyl]-1-(tert-butyloxycarbonyl)piperidine-3-carboxylic acid in 50-cm³ of methanol was cooled to a temperature in the region of −25° C. with stirring and under an inert atmosphere. 1.6-cm³ of thionyl chloride were added to this solution over 25 minutes. The mixture was brought to a temperature in the region of 20° C., while the stirring was continued for a further 48 hours. The reaction mixture was concentrated under reduced pressure (5 kPa) at a temperature in the region of 40° C., taken up in 100-cm³ of toluene and the mixture was again concentrated-under reduced pressure (5 kPa). The residue was taken up in 50-cm³ of diisopropyl ether, triturated and concentrated to dryness under reduced pressure (5 kPa). 1.17 g of methyl (3RS,4RS)-4-[3-(R,S)-hydroxy-3-(3-fluoro-6-methoxyquinolin-4-yl)propyl]piperidine-3-carboxylate dihydrochloride were obtained in the form of a yellow powder.

Infrared spectrum (KBr tablet):3415; 3129; 2949; 2772; 2473; 2022; 1733; 1622; 1603; 1555; 1496; 1420; 1307; 1242; 1172; 1019; 871 and 795 cm-1 d) (3RS,4RS)-4-[3-(R,S)-hydroxy-3-(3-fluoro-6-methoxyquinolin-4-yl)propyl]-1-(tert-butyloxycarbonyl)piperdine-3-carboxylic Acid A solution of 1.77 g of methyl (3RS,4RS)-4-[3-(3-fluoro-6-methoxyquinolin-4-yl)-3-propyl]-1-(tert-butyloxycarbonyl)piperidine-3-carboxylate, 140-cm³ of anhydrous dimethyl sulfoxide and 30-cm³ of anhydrous tert-butanol was stirred under an inert atmosphere free of water at 20° C. This solution was purged with pure oxygen until the reaction mixture becomes saturated. A solution containing 1.75 g of potassium tert-butoxide in 10-cm³ of anhydrous tert-butanol was then added. Oxygen was again introduced by bubbling for a further 1 hour and 10 minutes with vigorous stirring. The solution obtained was purged with nitrogen and then cooled to 0° C. 1-cm³ of pure acetic acid in 100-cm³ of water was then added followed by 100-cm³ of water and 500-cm³ of ether. The organic phase was separated after settling out, washed 7 times with 100-cm³ of water and 3 times with 100-cm³ of a saturated aqueous sodium chloride solution. The aqueous phase was extracted with 400-cm³ of ethyl acetate, washed 7 times with 75-cm³ of water and 3 times with 75-cm³ of a saturated aqueous sodium chloride solution. The 2 organic phases were combined, dried over magnesium sulfate, filtered and concentrated to dryness under reduced pressure (5 kPa) at a temperature in the region of 40° C. 1.26 g of (3RS,4RS)-4-[3-(R,S)-hydroxy-3-(3-fluoro-6-methoxyquinolin-4-yl)propyl]-1-(tert-butyloxycarbonyl)piperidine-3-carboxylic acid were obtained in the form of a white foam.

¹H NMR spectrum (400 MHz, (CD3)₂SO d6 with, at a temperature of 383 K, δ in ppm). A mixture of stereoisomers was observed.

\* from 0.85 to 2.30 (mt: 16H); from 2.60 to 3.25 (mt: 5H); 3.88 (mt: 1H); 3.94 (s: 3H); 4.00 (broad dd, J=14 and 3 Hz: 1H); 5.35 (mt: 1H); 7.38 (mt: 1H); from 7.90 to 8.00 (mt: 2H); 8.63 (broad s: 1H).

e) Methyl (3RS,4RS)-4-[3-(3-fluoro-6-methoxyquinolin-4-yl)-3-propyl]-1-(tert-butyloxycarbonyl)piperdine-3-carboxylate A solution of 1.45 g of methyl (3RS,4RS)-1-(tert-butyloxycarbonyl)-4-allylpiperidine-3-carboxylate in 20-cm³ of tetrahydrofuran was slowly added, at a temperature in the region of 0° C. with stirring and under an inert atmosphere, to 16-cm³ of a 0.5 M solution of 9-borabicyclo[3.3.1]nonane in tetrahydrofuran. The mixture was then brought to a temperature in the region of 20° C. while the stirring was continued for a further 4 hours. 1.52 g of 4-iodo-3-fluoro-6-methoxyquinoline in solution in 40 cm³ of tetrahydrofuran were added, followed by 100 mg of palladiumdiphenylphosphinoferrocene chloride and finally 3.18 g of tribasic potassium phosphate. The reaction mixture was heated for 15 hours under reflux and then filtered in the hot state on sintered glass. The filtrate was taken up in 50-cm³ of ethyl acetate and concentrated to dryness under reduced pressure (5 kPa). The residue was taken up in 75-cm of ethyl acetate and 40-cm³ of water. The organic phase was separated after settling out, washed twice with 40-cm³ of a saturated aqueous sodium chloride solution, dried over magnesium sulfate, filtered and then concentrated under reduced pressure (5 kPa) at a temperature in the region of 40° C. The residue was purified by chromatography, under a nitrogen pressure of 50 kPa, on a column of silica gel (particle size 20–45μ; diameter 2.5 cm; height 40 cm), eluting with a mixture of cyclohexane-ethyl acetate (75/25 by volume) and collecting 50-cm³ fractions. Fractions 16 to 22 were combined and then concentrated. 1.77 g of methyl (3RS,4RS)-4-[3-(3-fluoro-6-methoxyquinolin-4-yl)-3- propyl]-1-(tert-butyloxycarbonyl)piperidine-3-carboxylate were obtained in the form of a colorless oil.

¹H NMR spectrum (300 MHz, (CD₃)₂SO d6 with, δ in ppm): from 1.25 to 1.90 (mt: 16H); 2.61 (mt: 1H); from 2.65 to 3.25 (mt: 4H); 3.47 (broad s: 3H); from 3.60 to 4.05 (mt: 2H); 3.96 (s: 3H);7.36 (d, J=3 Hz: 1H); 7.40 (dd, J=9 and 3 Hz: 1H); 7.97 (d, J=9 Hz: 1H); 8.70 (broad s: 1H).

f) Methyl (3RS,4RS)-1-(tert-butyloxycarbonyl)-4-allylpiperidine-3-carboxylate 11.34 g of tributyltin hydride were added to a solution of 10.1 g of methyl 1-(tert-butyloxycarbonyl)-4-allyl-4-(methoxallyl)hydroxypiperidine-3-carboxylate in 250-cm³ of toluene under an inert atmosphere and at a temperature close to 20° C. 25 mg of AIBN were then added and the reaction mixture was heated at the reflux temperature of the solvent for 1 hour. The mixture was cooled to a temperature close to 20° C., concentrated to dryness under reduced pressure (5 kPa). The residue was taken up in 50-cm³ of dichloromethane and then purified by chromatography, under a nitrogen pressure of 50 kPa, on a column of silica gel (particle size 20–45μ; diameter 7 cm; height 40 cm), eluting with a mixture of cyclohexane-ethyl acetate (75/25 by volume) and collecting 200-cm³ fractions. Fractions 6 to 8 were combined, and then concentrated. 1.4 g of methyl (3RS,4RS)-1-(tert-butyloxycarbonyl)-4-allylpiperidine-3-carboxylate were obtained in the form of a colorless oil.

¹H NMR spectrum (400 MHz, (CD₃)₂SO d6 with, at a temperature of 353 K, δ in ppm): from 1.35 to 1.50 (mt: 1H); 1.40 (s: 9H); from 1.65 to 1.80 (mt,: 1H); 1.89 (mt: 1H); from 1.95 to 2.20 (mt: 2H); 2.62 (mt: 1H); 2.97 (mt: 1H); 3.22 (dd, J=14 and 4 Hz: 1H); 3.60 (s: 3H); from 3.65 to 3.80 (mt: 1H); 3.91 (broad dd, J=14 and 5 Hz: 1H); 5.02 (mt: 2H); from 5.65 to 5.85 (mt: 1H).

g) Methyl 1-(tert-butyloxycarbonyl)-4-allyl-4(methoxallyl)hydroxypiperidine-3-carboxylate 7.57 g of dimethylaminopyridine were added, under an inert atmosphere, to a solution of 9.4 g of methyl 1-(tert-butyloxycarbonyl)-4-allyl-4-hydroxypiperidine-3-carboxylate in 120-cm³ of acetonitrile and then 5.7-cm³ of oxalyl chloride were poured in over 20 minutes. After stirring for 15 hours at a temperature close to 20° C., 1.22 g of dimethylaminopyridine were added followed by 0.92-cm³ of oxalyl chloride. The stirring was maintained for 15 hours at the same temperature. This addition procedure was repeated once more and the stirring was continued for 6 hours. The reaction mixture was taken up in 200-cm³ of ethyl acetate and 200-cm³ of a saturated aqueous sodium bicarbonate solution. The organic phase was separated after settling out, washed with twice 100-cm³ of a saturated aqueous sodium chloride solution, dried over magnesium sulfate, and filtered on sintered glass. The filtrate was stirred for one hour with 11 g of silica, filtered on sintered glass, taken up in 20 g of silica and 300-cm³ of ethyl acetate, and then concentrated under reduced pressure (5 kPa) at a temperature, in the region of 40° C. 12.15 g of methyl 1-(tert-butyloxycarbonyl)-4-allyl-4-(methoxallyl)hydroxypiperidine-3-carboxylate were obtained in the form of a beige oil.

Infrared spectrum (CCl₄): 3082; 2980; 2954; 1775; 1748; 1699; 1641; 1424; 1392; 1367; 1245; 1202; 1162; 1142; 993 and 925 cm-1 h) Methyl 1-(tert-butyloxycarbonyl)-4-allyl-4-hydroxypiperidine-3-carboxylate 101.66 g of methyl 1-(tert-butyloxycarbonyl)-4-oxopiperidine-3-carboxylate were added, under an inert atmosphere and at a temperature close to 20° C., to 2.156 liters of a saturated aqueous solution of ammonium chloride and of THF (10/1 by volume) of THF. 34.73-cm³ of allyl bromide were then added, followed by 77.51 g of zinc while maintaining the temperature below 30° C. A solution of 69.47-cm³ of allyl bromide in 50-cm³ of THF was then poured in dropwise. After stirring for 3 hours at a temperature close to 20° C., the reaction was incomplete. 77.51 g of zinc were again added and then 104-cm³ of allyl bromide were poured in dropwise while the temperature was maintained below 30° C. The stirring was maintained at a temperature close to 20° C. for 15 hours, after which the reaction was still incomplete. 35 g of zinc were again added and then 55-cm³ of allyl bromide were poured in dropwise while the temperature was maintained below 30° C. The stirring was maintained at a temperature close to 20° C. for 4 hours, after which the reaction was still incomplete. 10 g of zinc were again added and then 25-cm³ of allyl bromide were poured in dropwise while the temperature was maintained below 30° C. The stirring was maintained at a temperature close to 20° C. for 2 hours. The reaction mixture was taken up in 900-cm³ of a 1 N HCl solution and 2 liters of ethyl ether and filtered on sintered glass. The filtrate was washed with 3 times 500-cm³ of etyl ether. The organic phase was washed with a saturated aqueous sodium chloride solution, dried over magnesium sulfate and concentrated to dryness under reduced pressure (5 kPa). A yellow oil was obtained, which was purified by chromatography, under a nitrogen pressure of 50 kPa, on a column of silica gel (particle size 20–45μ; diameter 12 cm; height 60 cm), eluting with a mixture of cyclohexane-ethyl acetate (80/20 by volume) and collecting 200-cm³ fractions. Fractions 51 to 75 were combined and then concentrated. 63.5 g of methyl 1-(tert-butyloxycarbonyl)-4-allyl-4-hydroxypiperidine-3-carboxylate were obtained in the form of a light yellow oil.

Infrared spectrum (CCl₄): 3513; 3078; 2980; 2954; 1697; 1641; 1423; 1392; 1366; 1200; 1163; 962 and 919 cm-1 i) Methyl 1-(tert-butyloxycarbonyl)-4-oxopiperidine-3-carboxylate 65.27-cm³ of trietylamine were added, with stirring, to a suspension of 89.93 g of 3-methoxycarbonyl-4-piperidone hydrochloride (at 98% purity) in 900-cm³ of dichloromethane, cooled to a temperature in the region of 0° C., followed by 91.12 g of di-tert-butyl dicarbonate solubilized beforehand in 400-cm³ of dichloromethane. The mixture was stirred for 12 hours at a temperature close to 20° C. The triethylamine hydrochloride was filtered, and then the filtrate was washed 3 times with 500-cm³ of water and then twice with 500-cm³ of a saturated aqueous sodium chloride solution. The organic phase was filtered on sintered material containing fine silica, dried over sodium sulfate, filtered and then concentrated under reduced pressure (5 kPa) at a temperature in the region of 40° C. 101.66 g of methyl 1-(tert-butyloxycarbonyl)-4-oxopiperidine-3-carboxylate were obtained in the form of a light yellow oil.

Infrared spectrum (CH₂Cl₂): 2982; 2932; 2872; 1740; 1691; 1664; 1622; 1477; 1468; 1423; 1367; 1338; 1309; 1235; 1200; 1167; 1123; 1064 cm⁻¹

Another embodiment of the present invention relates to the pharmaceutical compositions comprising at least one quinolylpropylpiperidine derivative or compound according to the invention, where appropriate in the form of a salt, in the pure state or in the form of a combination with one or more compatible and pharmaceutically acceptable diluents or adjuvants.

The compositions according to the invention may be used orally, parenterally, topically, rectally, or as aerosols.

As solid compositions for oral administration, tablets, pills, gelatin capsules, powders, or granules may be used. In these compositions, the active product according to the invention can be mixed with one or more inert diluents or adjuvants such as sucrose, lactose, or starch. These compositions may comprise substances other than the diluents, for example, a lubricant such as magnesium stearate or a coating intended for a controlled release.

As liquid compositions for oral administration, solutions that were pharmaceutically acceptable, suspensions, emulsions, syrups and elixirs containing inert diluents such as water or paraffin oil may be used. These compositions may also comprise substances other than the diluents, for example, wetting products, sweeteners, or flavorings.

The compositions for parenteral administration may be sterile solutions or emulsions. As solvents or vehicles, water, propylene glycol, polyethylene glycol, vegetable oils, for example, olive oil, injectable organic esters, for example ethyl oleate, may be used. These compositions may also contain adjuvants, for example, wetting, isotonizing, emulsifying, dispersing and stabilizing agents.

The sterilization may be carried out in several ways, for example with the aid of a bacteriological filter, by irradiation or by heating. They may also be prepared in the form of sterile solid compositions, which may be dissolved at the time of use in sterile water or any other injectable sterile medium.

The compositions for topical administration may be, for example, creams, ointments, lotions or aerosols.

The compositions for rectal administration include suppositories or rectal capsules, which contain, in addition to the active ingredient, excipients such as cocoa butter, semi-synthetic glycerides, or polyethylene glycols.

The compositions may also be aerosols. For use in the form of liquid aerosols, the compositions may be stable sterile solutions or solid compositions dissolved at the time of use in pyrogen-free sterile water, in saline, or any other pharmaceutically acceptable vehicle. For use in the form of dry aerosols intended to be directly inhaled, the active ingredient may be finely divided and combined with a water-soluble solid diluent or vehicle having a particle size of 30 to 80 µm, for example dextran, mannitol or lactose.

In human therapy, the novel quinolylpropylpiperidine derivatives or compounds according to the invention are useful in the treatment of infections of bacterial origin. The doses depend on the desired effect and on the duration of the treatment. The doctor will determine the dosage judged to be most appropriate according to the treatment, according to the age, weight, degree of the infection, and other factors specific to the subject to be treated. Generally, the doses range from 750 mg to 3 g of active product in 2 or 3 doses per day by the oral route or from 400 mg to 1.2 g by the intravenous route for an adult.

As used here, treatment includes therapy for a particular disease, such as treating an infection. In this respect, treatment can mean successfully eliminating the infection, reducing the effects associated with it, and/or reducing its severity. Treatment also includes prevention and prophylaxis of the onset of an infection by treating patients before an infection occurs, for example in the case of patients with wounds, burns, lesions, etc.

An effective amount of a compound of the invention is an amount sufficient to bring about a desired effect. For example, in the context of treating an infection, an effective amount of a compound of the invention would constitute an amount sufficient to achieve any of the effects described above under treatment of an infection or disease.

The following example illustrates a composition according to the invention.

Example A

A liquid composition intended for parenteral use was prepared according to customary techniques, comprising:

| | |
|---|---|
| (3RS,4RS)-4-[3-(3-fluoro-6-methoxyquinolin-4-yl)propyl]-1-[2-(thien-2-yl)thioethyl]piperidine-3-acetic acid dihydrochloride | 125 mg |
| glucose qs 5% | |
| sodium hydroxide qs pH = 4–4.5 | |
| water for injection | qs 50 ml |

Example B

A liquid composition intended for parenteral use was prepared according to customary techniques, comprising:

| | |
|---|---|
| (3RS,4RS)-4-[3-(R,S)-hydroxy-3-(3-fluoro-6-methoxyquinolin-4-yl)propyl]-1-[2-(2-thienylthio)ethyl]piperidine-3-acetic acid dihydrochloride | 125 mg |
| glucose qs 5% | |
| sodium hydroxide qs pH = 4–4.5 | |
| water for injection | qs 50 ml |

We claim:

1. A compound of formula (II)

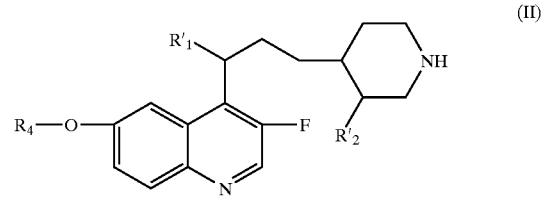

wherein $R'_1$ represents a hydrogen atom or a hydroxyl radical;

$R'_2$ represents a protected carboxyl or carboxymethyl radical; and $R_4$ represents an alkyl radical containing 1 to 6 carbon atoms, an alkenyl-$CH_2$—, alkynyl-$CH_2$—, cycloalkyl, or cycloalkylalkyl radical, wherein the alkenyl and alkynyl portions contain 2 to 6 carbon atoms and the cycloalkyl portions contain 3 to 8 carbon atoms, or a diastereoisomeric form, a cis form, or a trans form of a compound of formula (II), or a salt of any of the foregoing.

2. The compound of formula (II) as set forth in claim 1, wherein $R'_1$ represents a hydroxyl radical.

3. The compound of formula (II) as set forth in claim 1, wherein $R'_2$ represents a hydrolyzable ester of the carboxyl or carboxymethyl radical.

4. The compound of formula (II) as set forth in claim 1, wherein $R_4$ represents methyl.

5. A compound of the formula (III)

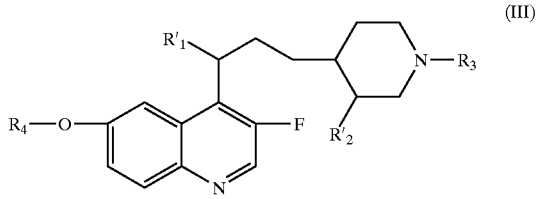

wherein
$R'_1$ represents a hydrogen atom or a hydroxyl radical;
$R'_2$ represents a protected carboxyl or carboxymethyl radical;
$R_3$ represents an alkyl radical having 1 to 6 carbon atoms, which is substituted with:
  a phenylthio radical, which is optionally substituted with 1 to 4 substituents chosen from halogen, hydroxyl, alkyl, alkyloxy, trifluoromethyl, trifluoromethoxy, carboxyl, alkyloxycarbonyl, cyano, and amino,
  a cycloalkylthio radical in which the cyclic portion contains 3 to 7 members, or
  a 5- to 6-membered aromatic heterocyclylthio radical with 1 to 4 heteroatoms chosen from nitrogen, oxygen, and sulfur, and wherein the 5- to 6-membered aromatic heterocyclylthio radical is optionally substituted with at least one radical chosen from halogen, hydroxyl, alkyl, alkyloxy, trifluoromethyl, trifluoro-methoxy, oxo, carboxyl, alkyloxycarbonyl, cyano, and amino; or
$R_3$ represents a propargyl radical substituted with:
  a phenyl radical, which is optionally substituted with 1 to 4 substituents chosen from halogen, hydroxyl, alkyl, alkyloxy, trifluoromethyl, trifluoromethoxy, carboxyl, alkyloxycarbonyl, cyano, and amino,
  a 3- to 7-membered cycloalkyl radical, or
  a 5- to 6-membered aromatic heterocyclyl radical with 1 to 4 heteroatoms chosen from nitrogen, oxygen, and sulfur, and wherein the 5- to 6-membered aromatic heterocyclyl radical is optionally substituted with at least one radical chosen from halogen, hydroxyl, alkyl, alkyloxy, trifluoromethyl, trifluoromethoxy, oxo, carboxyl, alkyloxycarbonyl, cyano, and amino; and
$R_4$ represents an alkyl radical containing 1 to 6 carbon atoms, an alkenyl-$CH_2$—, alkynyl-$CH_2$—, cycloalkyl, or cycloalkylalkyl radical, wherein the alkenyl and alkynyl portions contain 2 to 6 carbon atoms and the cycloalkyl portions contain 3 to 8 carbon atoms,
or a diasterecisomeric form, a cis form, or a trans form of a compound of formula (III), or a salt of any of the foregoing.

6. The compound of formula (III) as claimed in claim 5, wherein $R'_1$ represents a hydroxyl radical.

7. The compound of formula (III) as claimed in claim 5, wherein $R'_2$ represents a hydrolyzable ester of the carboxyl or carboxymethyl radical.

8. The compound of formula (III) as claimed in claim 5, wherein $R_3$ represents an alkyl radical substituted with the optionally substituted phenylthio radical, the cycloalkylthio radical, or the optionally substituted heterocyclylthio radical.

9. The compound of formula (III) as claimed in claim 5, wherein $R_3$ represents a propargyl radical substituted with the optionally substituted phenyl radical, the cycloalkyl radical, or the optionally substituted heterocyclyl radical.

10. The compound of formula (III) as claimed in claim 5, wherein $R_4$ represents methyl.

11. A process for preparing a compound as claimed in claim 1, comprising: selectively hydrogenating a quinolyl-propylpiperidine derivative of formula (VI):

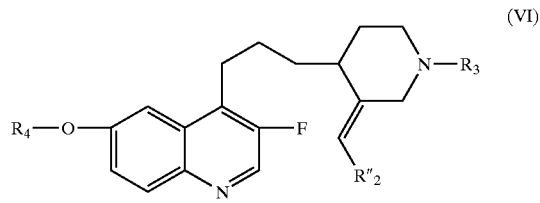

wherein $R_4$ is as defined in claim 1, wherein $R''_2$ is the protected radical corresponding to $R'_2$, and wherein the amine functional group of the piperidine in said derivative of formula (VI) is protected before the selective hydrogenation reaction, and
deprotecting the amine functional group of the piperidine, wherein $R'_2$ in the compound as claimed in claim 1 is a protected carboxymethyl radical, and
wherein $R'_1$ in the compound as claimed in claim 1 is a hydrogen, and optionally, converting the resulting compound into a salt.

12. A process according to the claim 11, wherein the amine functional group of the piperidine is protected with a benzyloxycarbonyl radical.

13. A process according to claim 11, wherein $R'_2$ represents a hydrolyzable ester of the carboxymethyl radical.

14. A process according to claim 11, wherein $R_4$ represents methyl.

15. A process for preparing a compound as claimed in claim 1, comprising: condensing a quinoline derivative of formula (VII),

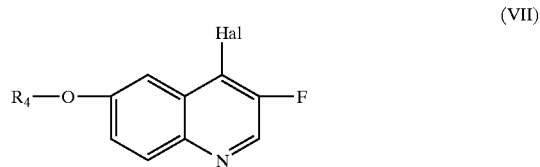

wherein $R_4$ is as defined in claim 1, and Hal represents an iodine or bromine atom,
with a piperidine derivative of formula (X),

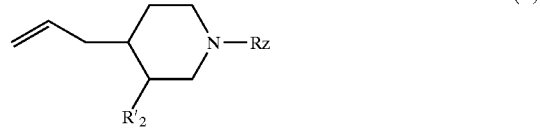

wherein Rz represents an amino-protecting radical, and removing the amino-protecting radical Rz,
wherein $R'_2$ in the compound as claimed in claim 1 is a protected carboxyl radical and $R'_1$ is a hydrogen, and optionally, converting the resulting compound into a salt.

16. A process according to claim 15, wherein $R'_2$ represents a hydrolyzable ester of the carboxyl radical.

17. A process according to claim 15, wherein $R_4$ represents methyl.

18. A process for preparing a compound as claimed in claim 1 wherein $R'_1$ is a hydroxyl radical, comprising:
a oxidizing the corresponding derivative for which $R'_1$ is a hydrogen atom, and
optionally, converting the resulting compound into a salt.

19. A process according to claim 18, wherein $R'_2$ in the compound as claimed in claim 1, represents a hydrolyzable ester of a carboxymethyl radical.

20. A process according to claim 18, wherein $R'_2$ in the compound as claimed in claim 1, represents a hydrolyzable ester of a carboxyl radical.

21. A process according to claim 18, wherein $R_4$ represents methyl.

22. A process for preparing a compound as claimed in claim 5, comprising condensing an $R_3$ radical with a quinolylpropylpiperidine derivative of formula (II):

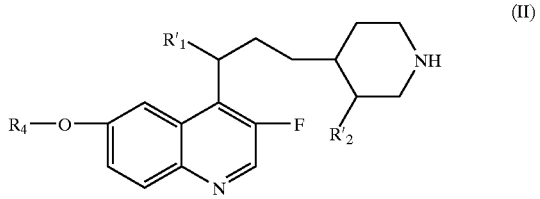

in which $R'_1, R'_2, R_3$, and $R_4$ are as defined in claim 5, and optionally converting the resulting compound into a salt.

23. A process according to claim 22, wherein $R'_1$ represents a hydroxyl radical.

24. A process according to claim 22, wherein $R'_2$ represents a hydrolyzable ester of the carboxyl or carboxymethyl radical.

25. A process according to claim 22, wherein $R_3$ represents an alkyl radical substituted with the optionally substituted phenylthio radical, the cycloalkylthio radical, or the optionally substituted heterocyclylthio radical.

26. A process according to claim 22, wherein $R_3$ represents a propargyl radical substituted with the optionally substituted phenyl radical, the cycloalkyl radical, or the optionally substituted heterocyclyl radical.

27. A process according to claim 22, wherein $R_4$ represents methyl.

* * * * *